(12) United States Patent
de Waal Malefyt et al.

(10) Patent No.: US 6,797,813 B2
(45) Date of Patent: Sep. 28, 2004

(54) AK155 ANTIBODIES AND BINDING FRAGMENTS THEREOF

(75) Inventors: Rene de Waal Malefyt, Sunnyvale, CA (US); Helmut Flickensher, Heidelberg (DE); Bernhard Fleckenstein, Wiesenthau (DE); Andrea Knappe, München (DE)

(73) Assignee: Schering Corporation, Kenilworth, NJ (US)

( * ) Notice: Subject to any disclaimer, the term of this patent is extended or adjusted under 35 U.S.C. 154(b) by 233 days.

(21) Appl. No.: 10/083,720

(22) Filed: Feb. 28, 2002

(65) Prior Publication Data

US 2003/0073199 A1 Apr. 17, 2003

Related U.S. Application Data

(60) Continuation-in-part of application No. 09/363,993, filed on Jul. 29, 1999, now abandoned, which is a division of application No. 08/934,959, filed on Sep. 22, 1997, now Pat. No. 5,989,867.
(60) Provisional application No. 60/345,690, filed on Jan. 3, 2002, provisional application No. 60/302,176, filed on Jun. 28, 2001, and provisional application No. 60/027,368, filed on Sep. 23, 1996.

(51) Int. Cl.[7] .............................................. C07K 16/24
(52) U.S. Cl. ............................. 530/388.23; 530/387.1; 530/389.1; 530/388.1; 530/387.3; 530/388.15; 530/389.2; 424/1.11; 424/1.49
(58) Field of Search .......................... 530/387.1, 389.1, 530/388.1, 387.3, 388.15, 388.23, 389.2; 424/1.11, 1.49

(56) References Cited

U.S. PATENT DOCUMENTS 5,231,012 A 7/1993 Mosmann et al. ....... 435/69.52

OTHER PUBLICATIONS

M.D. Adams, et al., *GenBank*, Accession No. B69652, Dec. 8, 1997. Definition: "RPCI11–5J6.TVB RPCI–11 *Homo sapiens* genomic clone RPCI–11–5J6, genomic survey sequence.".

M.D. Adams, et al., *GenBank*, Accession No. B48149, Nov. 10, 1997. Definition: "RPCI11–5J6.TV RPCI–11 *Homo sapiens* genomic clone RPCI–11–5J6, genomic survey sequence.".

Jan E. de Vries and Rene de Waal Malefyt, *Interleukin 10*, R.G. Landes Company: Austin, Texas, 1995.

G.S. Hudson, et al., *GenBank*, Accession No. M11924, Sep. 1, 1988. Definition: "Epstein–Barr virus B95–8, 12kb short unique region.".

Helene M. Martin, et al., *Gene*, 159(2):187–191, 1995. "Cloning and characterisation of an ovine interleukin–10–encoding cDNA".

Anthony R. Mire–Sluis, et al., *Journal of Immunological Methods*, 187(2):191–199, 1995. "Quantitative cell line based bioassays for human cytokines".

Kevin W. Moore, et al., *GenBank*, Accession No. M37897, Jun. 12, 1991. Definition: "Mouse interleukin 10 mRNA, complete cds.".

H.–J.Rode, et al., *GenBank*, Accession No. L08504, Aug. 2, 1993. Definition: "Equine herpesvirus type 2 interleukin 10–like gene, complete cds.".

P. Vieira, et al., *GenBank*, Accession No. M57627, Mar. 7, 1995. Definition: "Human interleukin 10 (IL 10) mRNA, complete cds.".

*Primary Examiner*—Prema Mertz
(74) *Attorney, Agent, or Firm*—Edwin P. Ching; Sheela Mohan-Peterson

(57) ABSTRACT

Purified genes encoding a cytokine from a mammal, reagents related thereto including purified proteins, specific antibodies, and nucleic acids encoding this molecule are provided. Methods of using these reagents and diagnostic kits are also provided.

17 Claims, No Drawings

US 6,797,813 B2

AK155 ANTIBODIES AND BINDING FRAGMENTS THEREOF

This filing is a Continuation-in-Part of patent application U.S. Ser. No. 09/363,993, filed Jul. 29, 1999, now abandoned which is a divisional of U.S. Ser. No. 08/934,959, filed Sep. 22, 1997, now U.S. Pat. No. 5,989,867, issued Nov. 23, 1999, which claims benefit of U.S. provisional patent applications 60/345,690, filed Jan. 3, 2002, No. 60/302,176, filed Jun. 28, 2001 and 60/027,368, filed Sep. 23, 1996, all of which are incorporated herein by reference.

FIELD OF THE INVENTION

The present invention pertains to compositions related to proteins which function in controlling biology and physiology of mammalian cells, e.g., cells of a mammalian immune system. In particular, it provides purified genes, proteins, antibodies, and related reagents useful, e.g., to regulate activation, development, differentiation, and function of various cell types, including hematopoietic cells.

BACKGROUND OF THE INVENTION

AK155 is a cytokine that is structurally related to interleukin-10 (IL-10). A number of cytokines have been classed as IL-10-like, based on their structure. The IL-10-like cytokines include IL-20, IL-22, and mda-7, as well as AK155 (Moore, et al., (2001) *Annu. Rev. Immunol.* 19:683–765; Moore, et al. (1993) *Annu. Rev. Immunol.* 11:165–190). Cytokines are signaling molecules that mediate communication between cells, e.g., between cells of the immune system. Once secreted, cytokines travel to a different or identical cell, bind to a membrane-bound receptor, and provoke a series of events such as protein phosphorylation or gene activation, where these events result in changes in phagocytic or secretory activity, or changes in migration, differentiation state, and proliferation activity.

The cytokines may be classed into those associated with increased inflammation (Th1-type response) and decreased inflammation (Th2-type response). The Th1-type response is characterized by increases in production of interferon-γ (IFN-γ), tumor necrosis factor-α (TNF-α), TNF-β, IL-12, IL-18, and other pro-inflammatory cytokines (Sallusto, et al. (1998) *Immunol. Today* 19:568–574). IL-17 is generally a pro-inflammatory cytokine (Fort, et al. (2001) *J. Immunol.* 15:985–995). Th2-type response is characterized by increases in production of cytokines that suppress inflammation, e.g., IL-4, IL-5, IL-10, and IL-13 (Liu, et al. (2001) *Nature Immunol.* 2:585–589). IL-25 appears to suppress inflammation (Fort, et a. (2001) *J. Immunol.* 15:985–995).

Within one interleukin family, such as the IL-1 family, different interleukins may be functionally related to each other in that they influence the course of one event, but exert opposite effects on that event. For example, 1L-1ε has a pro-inflammatory effect, while IL-1δ has an anti-inflammatory effect (Debets, et al. (2001) *J. Immunol.* 167:1440–1446). IL-17 and IL-25 are examples of two other cytokines which are structurally similar, but produce opposite biological effects. The structure of any particular cytokine therefore serves as a guide to determining its physiological function.

An analysis of cell signaling proteins can also help determine a cytokine's role in physiology. For example, signaling involving signal transducers and activators of transcription-4 (STAT4) may indicate an inflammatory response, while signaling via STAT6 may indicate an anti-inflammatory response or Th2-type response (Romagnani (1997) *Immunol. Today* 18:263–266). Hence, the identities of the proteins that are phosphorylated, of the particular amino acid residues that become phosphorylated, and of the relevant transcription factors and genes that become activated, are all relevant to determining the function of the cytokine of interest. Other powerful techniques for determining the functions of cytokines and related signaling proteins include use of genetically altered animals where a specific gene is altered in all cells, e.g., IL-10$^{-/-}$ mice (Scheerens, et al., (2001) *Eur. J. Immunol.* 31:1465–1474), or where the genetic alteration is targeted to only one type of cell in the animal, e.g., liver cells, epithelial cells, cells of lymphoid lineage (Blumberg, et al., (2001) *Cell* 104:9–19), or macrophages and neutrophils (Takeda, et al. (1999) *Immunity* 10:39–49).

SUMMARY OF THE INVENTION

The present invention is directed to mammalian, e.g., rodent, canine, feline, primate, AK155 (interleukin-XX; IL-XX) and its biological activities. It includes nucleic acids coding for polypeptides themselves and methods for their production and use. The nucleic acids of the invention are characterized, in part, by their homology to cloned complementary DNA (cDNA) sequences enclosed herein, or by functional assays for IL-10-like activities of the polypeptides encoded by these nucleic acids. Methods for modulating, inhibiting, or stimulating an immune response are provided.

The present invention is based, in part, upon the discovery of a new cytokine exhibiting a sequence similarity to cellular IL-10. In particular, it provides a gene encoding a protein whose mature size is about 150 amino acids, which is expressed in virally transformed cells, and in certain tissues, e.g., kidney, and possibly lung and liver. Functional equivalents exhibiting significant sequence homology will be available from various mammalian species, i.e., human, mouse, rat.

More particularly, the present invention provides a substantially pure or recombinant AK155 protein or peptide fragment thereof. Various embodiments include an antigenic protein or peptide selected from a protein or peptide from a warm blooded animal selected from the group of birds and mammals, including a primate; a protein or peptide comprising at least one polypeptide segment of SEQ ID NO:2 or a fragment thereof; a protein or peptide which exhibits a post-translational modification pattern distinct from natural AK155; or a protein or peptide which is capable of co-stimulating a T cell with another signal. The protein or peptide can comprise a fusion protein. Another embodiment is a composition comprising an AK155 protein or peptide and a pharmaceutically acceptable carrier.

The invention also embraces an antibody which specifically binds a AK155 protein or peptide, e.g., wherein the AK155 is a mammalian protein, including a primate; the antibody is raised against a purified AK155 peptide sequence of SEQ ID NO:2; the antibody is a monoclonal antibody; or the antibody is labeled. The antibodies also make available a method of purifying an AK155 protein or peptide from other materials in a mixture comprising contacting the mixture to an anti-AK155 antibody, and separating bound AK155 from other materials.

Another aspect of the invention is an isolated or recombinant nucleic acid capable of encoding a full length or mature AK155 polypeptide, including a nucleic acid which encodes a sequence of SEQ ID NO:2; which includes a sequence of SEQ ID NO:1; or which encodes a sequence from a natural AK155. Such nucleic acid embodiments also include an expression vector.

The invention also provides a kit containing a substantially pure AK155 or fragment; an antibody or receptor which specifically binds AK155; or a nucleic acid, or its complement, encoding AK155 or a fragment thereof. This kit also provides methods for detecting in a sample the presence of a nucleic acid, protein, or antibody, comprising testing said sample with such a kit.

The invention also supplies methods of modulating the physiology of a cell comprising contacting said cell with a substantially pure AK155 or fragment; an antibody or binding partner which specifically binds an AK155; or a nucleic acid encoding an AK155 or peptide. Certain preferred embodiments include a method where the cell is a T cell and the modulating of physiology is activation of the T cell or apoptosis of the T cell; or where the cell is in a tissue or in an organism.

Also provided are methods of expressing an AK155 peptide by expressing a nucleic acid encoding an AK155 polypeptide. The invention also provides a cell, tissue, organ, or organism comprising a nucleic acid encoding an AK155 peptide.

The invention also provides a recombinant nucleic acid comprising sequence at least about 70% identity over a stretch of at least about 30 nucleotides to an AK155 nucleic acid sequence of SEQ ID NO:1, useful, e.g., as a probe or PCR primer for a related gene. Another embodiment further encodes a polypeptide comprising at least about 60% identity over a stretch of at least about 20 amino acids to an AK155 sequence of SEQ ID NO:2.

The invention further provides a method of treating a patient having an immune or inflammatory response by administering an effective dose of an antibody or binding partner specific for AK155; an AK155 protein or polypeptide; or a nucleic acid encoding an AK155 peptide.

DEFINITIONS

"AK155" refers to a polypeptide having a sequence that has greater than 70% amino acid sequence identity, preferably greater than 75%, 80%, 85%, 90%, or 95% amino acid sequence identity, to SEQ ID NO:2.

"AK155 receptor" refers to a polypeptide complex that is a comprised of an α-subunit and β-subunit. The term AK155 receptor therefore refers to polymorphic variants, alleles, mutants, and interspecies homologs that: (1) have the characteristic that they are activated by the binding of AK155; (2) bind to antibodies, e.g., polyclonal antibodies, raised against an immunogen comprising an amino acid sequence of the α-subunit or β-subunit of the AK155 receptor.

"Cytokines" are proteins that regulate and coordinate many of the activities of the immune system. Cytokines produced by mononuclear phagocytes have been called monokines, while those produced by lymphocytes have been called lymphokines. Most of the cytokines have numbered names while others have trivial names, such as interferon (IFN) and tumor necrosis factor (TNF) (Abbas, et al. (2000) Cellular and Molecular Immunology, 4$^{th}$ ed., W. B. Saunders Co., New York, N.Y., pp. 235, 486).

"IL-10-related cytokines" refers to cytokines with homology to IL-10. These cytokines include IL-20, IL-22, IL-19, melanoma differentiation-associated gene 7 (mda-7), and AK155 (Dumoutier, et al. (2001) J. Immunol. 167:3545–3549). The IL-10-related cytokines also include the IL-10 homologues of Epstein-Barr virus, equine herpesvirus type 2, and parapoxyirus (Knappe, et al. (2000) J. Virology 74:3881–3887).

"Recombinant" when used with reference, e.g., to a cell, or nucleic acid, protein, or vector, indicates that the cell, nucleic acid, protein or vector, has been modified by the introduction of an exogenous, non-native nucleic acid or the alteration of a native nucleic acid, or that the cell is derived from a cell so modified.

"Exogenous" refers to substances that are produced outside an organism or cell, depending on the context.

"Anti-inflammatory" refers to the reduction of inflammation, and includes reducing a local or systemic response to cellular injury that is marked by capillary dilation and leukocytic infilatration out of the capillaries and into the surrounding tissues. "Anti-inflammatory" also refers to the reduction of any of the classic signs of inflammation, i.e., rubor (redness), tumor (swelling), calor (heat), and dolor (pain).

"Functional effects" in the context of assays for testing compounds affecting a receptor comprising an AK155 receptor includes the determination of any parameter that is indirectly or directly under the influence of the receptor. It includes changes in the conformation of an AK155 receptor, changes in the strength or nature of association and binding of various proteins, cofactors, and ligands to an AK155 receptor, changes in the percentage of AK155 receptor that is cytosolic or membrane-bound, changes in amount of surface expression of AK155 receptor or in the amount of surface-association of proteins that bind to an AK155 receptor, changes in protein phosphorylation, in the rate of transcription of a gene, in the rate of secretion, in the rate of cell proliferation, and in cell maturation or differentiation.

"Inhibitors" and "activators" of the AK155 receptor refer to inhibitory or activating molecules, respectively, identified using in vitro and in vivo assays for AK155 receptor activation. A "modulator" of AK155 receptor activation is a molecule that is an inhibitor or an activator of AK155 receptor. Inhibitors are compounds that decrease, block, prevent, delay activation, inactivate, desensitize, or down regulate the receptor. Activators are compounds that increase, activate, facilitate, enhance activation, sensitize or up regulate receptor activity. To examine the extent of inhibition, samples or assays comprising an AK155 receptor are treated with a potential activator or inhibitor and are compared to control samples without the inhibitor. Control samples (untreated with inhibitors) are assigned a relative AK155 receptor activity value of 100%. Inhibition of the AK155 receptor is achieved when the AK155 receptor activity value relative to the control is about 90%, preferably 50%, more preferably 5–25%. Activation of the AK155 receptor is achieved when the AK155 receptor activity value relative to the control is 110%, more preferably 150%, still more preferably at least 2-fold higher, and most preferrably at least 5-fold higher.

"Cell line" refers to a population of cells capable of continuous or prolonged growth and division in vitro. Often, cell lines are clonal populations derived from a single progenitor cell. Spontaneous or induced changes can occur in the genome can occur during storage or transfer of one or more cells present in the population of cells. Therefore, cells derived from a cell line may not be precisely identical to the ancestral cells or cultures, and the cell line includes such variants. The term "cell lines" also includes immortalized cells (U.S. Pat. No. 6,090,611 issued to Covacci, et al.).

By "purified" and "isolated" is meant, when referring to a polypeptide, that the polypeptide is present in the substantial absence of the other biological macromolecules of the same type. The term "purified" as used herein preferably means at least 85%, more preferably still at least 95% by weight, and most preferably at least 98% by weight, of biological macromolecules of the same type present. The weights of water, buffers, salts, detergents, reductants, protease inhibitors, stabilizers, excipients, and other small molecules, especially those having a molecular weight of less than 1000, are not used in the determination of polypeptide purity (U.S. Pat. No. 6,090,611 issued to Covacci, et al.). Purity and homogeneity are typically determined using sodium dodecyl sulfate polyacrylamide gel electrophoresis (SDS PAGE), optionally with analysis using a gel scanner (Brody, T. (1997) *Analyt. Biochem.* 247:247–256), high pressure liquid chromatography (HPLC) or capillary electrophoresis (CE) (Gooding and Regnier (2002) *HPLC of Biological Molecules,* 2nd ed., Marcel Dekker, NY; Cunico, Gooding, and Wehr (1998) *Basic HPLC and CE of Biomolecules,* Bay Biological Laboratory, Inc. Hercules, Calif.), and N-terminal (Abe, et al. (1998) *J. Biol. Chem.* 273:11150–11157) or C-terminal amino acid sequencing (Boyd, et al. (1992) *Analyt. Biochem.* 206:344–352). A protein that is the predominant species present in a preparation is substantially purified. It is understood that 100% purity may be an impossibility, e.g., because of low levels of trace amounts of proteases or natural deamidation (Hsu, et al. (1998) *Biochemistry* 37:2251–2262; Robinson and Robinson (2001) *Proc. Natl. Acad. Sci. USA* 98:12409–12413; Sarioglu, et al. (2000) *Electrophoresis* 21:2209–2218).

"Nucleic acid" refers to deoxyribonucleotides or ribonucleotides and polymers thereof in either single stranded or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., (1991) *Nucleic Acids Res.* 19:5081; Ohtsuka, et al. (1985) *J. Biol. Chem.* 260:2605–2608; Rossolini et al. (1994) *Mol. Cell. Probes* 8:91–98). The term nucleic acid is used interchangeably with gene, cDNA, mRNA, oligonucleotide, and polynucleotide.

A particular nucleic acid sequence also implicitly encompasses "allelic variants" and "splice variants." Similarly, a particular protein encoded by a nucleic acid implicitly encompasses any protein encoded by an allelic variant and splice variant of that nucleic acid. "Splice variants" are products of alternative splicing of a mRNA. After transcription, an initial mRNA may be spliced such that different (alternate) splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. It will be understood that inasmuch as natural allelic variations exist and occur from individual to individual, as demonstrated by amino acid differences in the overall sequence or by deletions, substitutions, insertions, inversions, or additions of one or more amino acids of said sequences, the present invention is intended to embrace all of such allelic variations of the two molecules involved. In addition, the location of and the degree of glycosylation depend upon the nature of the recombinant host organism employed as well as disease, i.e., rheumatic disease and rheumatoid arthritis, and such variations as may occur are included within the ambit of this invention (Jefferis (2001) *BioPharm* 14:19–27; Mimura, et al. (2001) *J. Biol. Chem.* 276:45539–45547; Axford (1999) *Biochim. Biophys. Acta* 1:219–229; Malhotra, et al. (1995) *Nature Med.* 1:237–243).

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, including selenomethionine, as well as those amino acids that are modified after incorporation into a polypeptide, e.g., hydroxyproline, γ-carboxyglutamate, O-phosphoserine, and cystine. Amino acid analogs refers to compounds that have the same basic chemical structure as a naturally occurring amino acid, i.e., an α-carbon that is bound by a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by their one-letter symbols.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a conserved amino acid or a small percentage of amino acids in the encoded sequence is a "conservatively modified variant." Conservative substitution tables providing functionally similar amino acids are well known in the art. An example of a conservative subtitution is the exchange of an amino acid in one of the following groups for another amino acid of the same group (U.S. Pat. No. 5,767,063 issued to Lee, et al.; Kyte and Doolittle (1982) *J. Mol. Biol.* 157:105–132):
(1) Hydrophobic: Norleucine, lie, Val, Leu, Phe; Cys; or Met;
(2) Neutral hydrophilic: Cys, Ser, Thr;
(3) Acidic: Asp, Glu;
(4) Basic: Asn, Gin, His, Lys, Arg;
(5) Residues that influence chain orientation: Gly; Pro.
(6) Aromatic: Trp; Tyr; Phe.
(7) Small amino acids: Gly, Ala, Ser.

For example, when no change or an insignificant change in biological function is desired, substitutions can be made by changing Val to Leu; Ser to Thr; or Asp to Glu.

Polypeptide molecules having substantially the same amino acid sequence as AK155 but possessing minor amino acid substitutions that do not substantially affect the functional aspects are within the definition of the contemplated invention. Variants with truncations or deletions of regions which do not change the biological functions of AK155 are also within the definition of the contemplated invention. Variants containing one or more peptide bond cleavages, where daughter polypeptides remain in association with each other, are within the definition of the contemplated invention. Where a polypeptide chain is cleaved, e.g., during normal processing or because of damage due to non-specific protease action, daughter polypeptides can maintain their association with each other because of covalent linkage via a disulfide bond or because of three dimensional conformations that allow or maintain a plurality of ionic bonds between the daughter polypeptides. Cleaved variants are contemplated, e.g., where cleavage results in a maintenance of antigenic activity or signal-transducing activity.

The term "protein" generally refers to the primary sequence of amino acids forming the polypeptide chain, any post-translational modifications of the proteins, dimers, and multimers of the polypeptide chain, and the three dimensional structure of the polypeptide. "Denatured protein" refers to a partially or totally denatured polypeptide, having some residual three dimensional structure or, alternatively, an essentially random three dimensional structure. When applied to a specific polypeptide, the term "protein" may or may not include covalent or non-covalent modifications, i.e., salts or cofactors associated with the protein, depending on the circumstances. For example, when a term refers to an aminotransferase, the term generally includes the non-covalently bound cofactor that is bound to the aminotransferase.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions, while an "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular open reading frame in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same i.e., 65%, 70%, 75%, 80%, 85%, 90%, 95%, or 100% identity over a specified region when compared and aligned for maximum correspondence over a comparison window, or designated region as measured using one of the following sequence comparison algorithms or by manual alignment and visual inspection. This definition also refers to the complement of a polynucleotide sequence.

Amino acid sequence homology, or sequence identity, is determined by optimizing residue matches, if necessary, by introducing gaps as required. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison*, Addison-Wesley, Reading, Mass.; and software packages, such as MacVector 7.1® from Accelrys, Inc. (San Diego, Calif.) and Vector NTI® Suite from InforMax, Inc. (Bethesda, Md.). "Sequence identity" means that in comparing two polypeptides, the identities of all of the corresponding amino acids in that stretch are one and the same, i.e., where there is a histidine in polypeptide A there is a histidine in polypeptide B. In determining a value for sequence identity, the amino acids of N-terminal or C-terminal extensions are ignored. "Sequence similarity" means that in comparing two polypeptides, the identities of all of the corresponding amino acids are one and the same, or correspond to a conservative substitution. Conservative substitutions are defined above in Definitions. Typical homologous proteins or peptides will have from 25–100% homology. Homology measures will be at least about 20%, generally at least about 30%, often at least about 40%, typically at least about 50%, usually at least about 60%, preferably at least about 70%, and more preferably at least about 80%.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to AK155 receptor nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. USA* 85:2444, by computerized implementations of these algorithms, as those provided by software packages, such as MacVector 7.1® from Accelrys, Inc. (San Diego, Calif.) and Vector NTI® Suite from InforMax, Inc. (Bethesda, Md.).

A preferred example of algorithm that is suitable for determining percent sequence identity and sequence similarity are the BLAST and BLAST 2.0 algorithms, which are described in Altschul, et al. (1977) *Nuc. Acids Res.* 25:3389–3402 and Altschul, et al. (1990) *J. Mol. Biol.* 215:403–410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information, on the world wide web at "ncbi.nlm.nih.gov." This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al. (1990) *J. Mol. Biol.* 215:403–410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff(1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions. Where the two polypeptides are substantially similar, 25% of the positions of non-identity are due to conservative changes, where more preferably 50% of the positions of non-identity are due to conservative changes, and still more preferably 90% of the positions of non-identity are due to conservative changes.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. A guide to the hybridization of nucleic acids is available (Tijssen (1993) *Laboratory Techniques in Biochemistry and Molecular Biology—Hybridization with Nucleic Probes*, Vol. 24, Parts 1 and 2, Elsevier, New York, N.Y.). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cased, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies occur as intact immunoglobulins, as fragments produced by digestion with various peptidases, or as recombinant varieties, such as humanized antibodies or single chain antibodies. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region.

In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). Suitable leucine zipper sequences include the jun and fos leucine zippers and the GCN4 leucine zipper (Kostelney, et al. (1992) J. Immunol. 148:1547–1553; U.S. Pat. No. 6,133,426 issued to Gonzalez, et al.).

While various antibody fragments are defined in terms of the digestion of an intact antibody, one of skill will appreciate that such fragments may be synthesized de novo either chemically or by using recombinant methodology. Thus, the term antibody, as used herein, also includes antibody fragments either produced by the modification of whole antibodies, or those synthesized de novo using recombinant methodologies, such as recombinant IgG antibodies (U.S. Pat. No. 4,816,567 issued to Cabilly, et al; U.S. Pat. No. 4,642,334; issued to Moore, et al.; Queen, et al. (1989) Proc. Natl Acad. Sci. USA 86:10029–10033), single chain antibodies, or antibodies acquired by phage display, and monoclonal antibodies made by the hybridoma method (Kohler, et al. (1975) Nature 256:495).

The synthesis of single chain antibodies is described in U.S. Pat. No. 4,946,778 issued to Ladner, et al., while single domain antibodies are described by Conrath, et al. (2001) J. Biol. Chem. 276:7346–7350, and Desmyter, et al. (2001) J. Biol. Chem. 276:26285–26290). Antibodies may also be produced by the phage display technique (Barbas, et al. (2001) Phage Display: A LaboratorY Manual, Cold Spring Harbor Laboratory, Cold Spring Harbor, N.Y.; Kay, et al. (1996) Phage Display of Peptides and Proteins: A Laboratory Manual, Academic Press, San Diego, Calif.; de Haard, et al. (1999) J. Biol. Chem. 274:18218–18230; McCafferty et al. (1990) Nature 348:552–554; Clackson et al. (1991) Nature 352:624–628; Marks et al. (1991) J. Mol. Biol. 222:581–597).

For preparation of monoclonal or polyclonal antibodies, any technique known in the art can be used (see, e.g., Kohler and Milstein (1975) Nature 256:495–497; Kozbor et al. (1983) Immunology Today 4:72; Cole et al. (1985) in Monoclonal Antibodies and Cancer Therapy, Alan R. Liss, Inc., New York, N.Y., pp. 77–96). Techniques for the production of single chain antibodies (U.S. Pat. No. 4,946,778 issued to Ladner, et al.) can be adapted to produce antibodies to polypeptides of this invention. Also, transgenic mice, or other organisms such as other mammals, may be used to express humanized antibodies.

An "anti-AK155 receptor antibody" is an antibody or antibody fragment that specifically binds an AK155 receptor or subunits thereof.

A "chimeric antibody" is an antibody molecule in which part or all of the constant region is altered, with a replacement or exchange, so that the antigen binding site is linked to a constant region of a different class or antibody, or to an enzyme, hormone, protein toxin (U.S. Pat. No. 6,051,405 issued to Fitzgerald, et al.), growth factor, or drug.

An "immunoassay" is an assay that uses an antibody to specifically bind an antigen. The immunoassay is characterized by the use of specific binding properties of a particular antibody to isolate, target, or quantify the antigen.

"Biological sample" as used herein is a sample of biological tissue or fluid that contains the AK155 receptor or nucleic acid encoding the subunits of the AK155 receptor proteins. Such samples include, but are not limited to, tissue isolated from humans. Biological samples may also include sections of tissues such as frozen sections taken for histologic purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

The phrase "specifically" or "selectively" binds, when referring to a ligand/receptor or other binding pair, refers to a binding reaction which is determinative of the presence of the protein in the presence of a heterogeneous population of proteins and other biologics. Thus, under designated conditions, a specified ligand binds to a particular receptor and does not bind in a significant amount to other proteins present in the sample.

In a preferred embodiment of the invention, AK155 or AK155 variant or mutein binds to an AK155 receptor or AK155 receptor subunit with an affinity that is ten times greater, more preferably 20-times greater, still more preferably 40-times, and most preferably 80-times greater than the affinity found when tested with any other proteins, aside from anti-AK155 antibodies.

In a preferred embodiment of the invention, anti-AK155 antibody binds to AK155, or a variant or mutein thereof, with an affinity that is ten times greater, more preferably 20-times greater, and still more preferably 40-times greater, and most preferably 80-times greater than the affinity with any other antibody. In a preferred embodiment of the monoclonal antibody to AK155, or to a variant or mutein thereof, the monoclonal antibody will have an affinity which is greater than about $10^9$ liters/mol, and preferably is equal to or greater than about $10^{10}$ liters/mol, as determined, for example, by Scatchard analysis (Munsen, et al (1980) *Analyt. Biochem.* 107:220–239). Further information on antibody affinity constants is available (Friguet, et al., (1985) *J. Immunol. Methods* 77:305; Hubble (1997) *Immunol. Today* 18:305–306).

"Ligand" refers to an entity that binds specifically to a polypeptide or a complex of more than one polypeptide. A "ligand binding domain" is a polypeptide or region of a polypeptide that is able to bind to said entity. A ligand may be a soluble protein, a membrane-associated protein, or an integral membrane-bound protein. Where a ligand binds to a receptor, the question of which molecule is the ligand and which molecule is the receptor can be determined on a case-by-case basis. Generally, where the binding event results in cell signaling, the entity (of the two entities being discussed) that is involved in downstream signaling is termed the "receptor." A freely diffusable and water-soluble entity that is involved in ligand/receptor interactions is usually a ligand, not a receptor.

An "agonist" is a compound that interacts with a target and causes an increase in the activation of the target.

An "antagonist" is a compound that opposes the actions of an agonist. An agonist prevents, inhibits, or neutralizes the activity of an agonist. An antagonist is also a compound that causes a decrease in activity of a target.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

"Monoclonal antibodies" also include clones of antigen-recognition and binding-site containing antibody fragments (Fv clones), i.e., isolated from phage antibody libraries.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. By assaying for the presence or absence of the probe, one can detect the presence or absence of the select sequence or subsequence.

A "labeled nucleic acid probe or oligonucleotide" is one that is modified, either covalently, through a linker or a chemical bond, or noncovalently, through ionic, van der Waals, electrostatic, or hydrogen bonds to a label such that the presence of the probe may be detected by detecting the presence of the label bound to the probe. The probes are preferably directly labeled as with isotopes, chromophores, fluorophores, chromogens, or indirectly labeled such as with biotin to which a streptavidin or avidin complex may later bind.

A composition is "labeled" that is detectable, either directly or indirectly, by spectroscopic, photochemical, biochemical, immunochemical, radiometric, or chemical means. For example, useful labels include $^{32}$P, fluorescent dyes, electron-dense reagents, enzymes and their substrates (e.g., as commonly used in enzyme-linked immunoassays, e.g., alkaline phosphatase and horse radish peroxidase), biotin-streptavidin, digoxigenin, or haptens and proteins for which antisera or monoclonal antibodies are available. The label or detectable moiety is typically bound, either covalently, through a linker or chemical bound, or through ionic, van der Waals or hydrogen bonds to the molecule to be detected.

The term "radiolabeled" refers to a compound to which a radioisotope has been attached through covalent or non-covalent means. Examples of radioisotopes include, without limitation, $^{3}$H, $^{14}$C, $^{32}$P, $^{33}$P, $^{35}$S, and $^{125}$I.

A "fluorophore" is a compound or moiety that accepts radiant energy of one wavelength and emits radiant energy of a second wavelength.

DETAILED DESCRIPTION

As used herein, including the appended claims, the singular forms of words such as "a," "an," and "the" include their corresponding plural references unless the context clearly dictates otherwise.

All references cited herein are incorporated herein by reference to the same extent as if each individual publication or patent application was specifically and individually indicated to be incorporated by reference.

OUTLINE

I. General.
II. Purified AK155.
 A. Physical properties.
 B. Biological properties.
III. Physical Variants.
 A. Sequence variants, fragments.
 B. Post-translational variants.
  1. Glycosylation.
  2. Others.
IV. Functional Variants.
 A. Analogs, fragments.
  1. Agonists.
  2. Antagonists.
 B. Mimetics.
  1. Protein.
  2. Chemicals.
 C. Species variants.
V. Antibodies.
 A. Polyclonal.
 B. Monoclonal.
 C. Fragments, single chain antibodies, binding compositions.

VI. Nucleic Acids.
A. Natural isolates; methods.
B. Synthetic genes.
C. Methods to isolate.
VII. Making AK155, mimetics.
A. Recombinant methods.
B. Synthetic methods.
C. Natural purification.
VIII. Uses
A. General; diagnostic; therapeutic.
B. Disease conditions.
C. IL-8 and inflammation.
D. STAT3 and inflammation.
E. Keratinocytes, ICAM-1, and inflammation.
F. IL-10 and inflammation.
G. B7-H1 and inflammation.
H. Drugs; anti-inflammatory; anti-neoplastic.
IX. Kits
A. Nucleic acid reagents.
B. Protein reagents.
C. Antibody reagents.
X. Isolating the AK155 receptor.

I. General

The present invention provides amino acid sequences and DNA sequences encoding various mammalian proteins which are cytokines. Full length cytokines, and fragments, or antagonists thereof will be useful in physiological modulation of cells expressing a receptor. It is likely that AK155 has either stimulatory or inhibitory effects on T cells, B cells, mast cells, natural killer (NK) cells, macrophages, monocytes, dendritic cells, eosinophils, thymocytes, and developmental precursors to the aforementioned cells. AK155 and fragments thereof will also be useful as antigens, that is, for raising antibodies to various epitopes on the protein, where these epitopes include linear and conformational epitopes.

A cDNA encoding AK155 was isolated from a virally infected cell. The AK155 cDNA contains a stretch of 510 bp in length and contained one large open reading frame encoding a small soluble cytokine-like protein. Structural features include an N-terminal leader sequence of about 21 amino acids, though the natural cleavage site may vary under different physiological conditions or with the host cell used, and may be on either side by a few residues. See Table 1 and SEQ ID NOs:1 and 2. AK155 exhibits structural motifs characteristic of cellular IL-10s from mouse and human, EBV viral IL-10, and the Equine herpesvirus IL-10. See Table 2. Table 3 represents nucleotide sequences which encode the protein sequence.

TABLE 1

Human AK155 nucleotide and predicted amino-acid sequence. Predicted leader sequence ends after about 21 amino acids, though natural boundaries may be different, also depending upon cell type. The standard domain boundaries to helix A correspond to residues about 16–39; α1 from about 47–55; helix B from about 81–100; α2 from about 110–123; and helix D from about 125–150. See SEQ ID NOs:1 and 2.

```
CTGTGAGTGA CACACGCTGA GTGGGGTGAA GGGAA ATG CTG GTG AAT TTC ATT         53
                                       Met Leu Val Asn Phe Ile
                                       -21 -20

TTG AGG TGT GGG TTG CTG TTA GTC ACT CTG TCT CTT GCC ATT GCC AAG        101
Leu Arg Cys Gly Leu Leu Leu Val Thr Leu Ser Leu Ala Ile Ala Lys
-15                 -10                 -5                    1

CAC AAG CAA TCT TCC TTC ACC AAA AGT TGT TAC CCA AGG GGA ACA TTG        149
His Lys Gln Ser Ser Phe Thr Lys Ser Cys Tyr Pro Arg Gly Thr Leu
/////////////5/////////////////10/////////////////15

TCC CAA GCT GTT GAC GCT CTC TAT ATC AAA GCA GCA TGG CTC AAA GCA        197
Ser Gln Ala Val Asp Ala Leu Tyr Ile Lys Ala Ala Trp Leu Lys Ala
              20                  25                  30

ACG ATT CCA GAA GAC CGC ATA AAA AAT ATA CGA TTA TTA AAA AAG AAA        245
Thr Ile Pro Glu Asp Arg Ile Lys Asn Ile Arg Leu Leu Lys Lys Lys
         35                  40                  45

ACA AAA AAG CAG TTT ATG AAA AAC TGT CAA TTT CAA GAA CAG CTT CTG        293
Thr Lys Lys Gln Phe Met Lys Asn Cys Gln Phe Gln Glu Gln Leu Leu
50                  55                  60                  65

TCC TTC TTC ATG GAA GAC GTT TTT GGT CAA CTG CAA TTG CAA GGC TGC        341
Ser Phe Phe Met Glu Asp Val Phe Gly Gln Leu Gln Leu Gln Gly Cys
              70                  75                  80

AAG AAA ATA CGC TTT GTG GAG GAC TTT CAT AGC CTT AGG CAG AAA TTG        389
Lys Lys Ile Arg Phe Val Glu Asp Phe His Ser Leu Arg Gln Lys Leu
              85                  90                  95

AGC CAC TGT ATT TCC TGT GCT TCA TCA GCT AGA GAG ATG AAA TCC ATT        437
Ser His Cys Ile Ser Cys Ala Ser Ser Ala Arg Glu Met Lys Ser Ile
              100                 105                 110
```

TABLE 1-continued

Human AK155 nucleotide and predicted amino-acid sequence. Predicted leader sequence ends after about 21 amino acids, though natural boundaries may be different, also depending upon cell type. The standard domain boundaries to helix A correspond to residues about 16–39; α1 from about 47–55; helix B from about 81–100; α2 from about 110–123; and helix D from about 125–150. See SEQ ID NOs:1 and 2.

```
ACC AGG ATG AAA AGA ATA TTT TAT AGG ATT GGA AAC AAA GGA ATC TAC      485
Thr Arg Met Lys Arg Ile Phe Tyr Arg Ile Gly Asn Lys Gly Ile Tyr
    115                 120                 125

AAA GCC ATC AGT GAA CTG GAT ATT CTT CTT TCC TGG ATT AAA AAA TTA      533
Lys Ala Ile Ser Glu Leu Asp Ile Leu Leu Ser Trp Ile Lys Lys Leu
130                 135                 140                 145

TTG GAA AGC AGT CAG TAAACCAAAG CCAAGTACAT TGATTTTACA GTTATTTGA       588
Leu Glu Ser Ser Gln
                150

AATACAATAA GAACTGCTAG AAATATGTTT ATAACAGTCT ATTTCTTTTA AAAACTTTTT    648

AACATAATAC TGACGGCATG TTAGGTGATT CAGAATAGAC AAGAAGGATT TAGTAAATTA    708

ACGTTTTGGA TATAAGTTGT CACTAATTTG CACATTTTCT GTGTTTTCAA ATAATGTTTC    768

CATTCTGAAC ATGTTTTGTC ATTCACAAGT ACATTGTGTC AACTTAATTT AAAGTATGTA    828

ACCTGAATTA ACTCGTGTAA TATTTGTGTG TGGAGTGGGA TGTGGGGGGT GGAGGGGGAA    888

TGACAGATTT CTGGAATGCA ATGTAATGTT ACTGAGACTT AAATAGATGT TATGTATATG    948

ATTGTCTGTT TAAGTGTTTG AAAATTGTTA ATTATGCCCA GTGTGAACTT AGTACTTAAC   1008

ACATTTTGAT TTTAATTAAA TAAATTGGGT TTCCTTCTCA AAAAAAAAAA AAAAAAAAAA   1068

AAAAAAAA                                                            1076
```

TABLE 2

Comparison of various IL-10 embodiments compared to AK155. First group is signal sequences, which are not aligned (Shown below are amino acid residues 1–18 of SEQ ID NO:3;1–23 of SEQ ID NO:4;1–18 of SEQ ID NO:5:1–18 of SEQ ID NO:6; and 1–21 of SEQ ID NO:2, respectively).

```
MFRASLLCCLVLLAGVWA                          Equine Herpes Virus (EHV)
MERRLVVTLQCLVLLYLAPECGG                     Epstein Barr Virus (EBV)
MPGSALLCCLLLLTGMRI                          moIL-10
MHSSALLCCLVLLTGVRA                          huIL-10
MLVNFILRCGLLLVTLSLAIA                       huAK155
```

(Shown below are amino acid residues 19–179 of SEQ ID NO:3; 24–170 of SEQ ID NO:4;19–178 of SEQ ID NO:5;19–178 of SEQ ID NO:6; and 22–171 of SEQ ID NO:2, respectively).

```
DNKYDSESGDDCPTLPTSLPHMLHELRAAFSRVKTFFQMKDQL    EHV
        TDQCDNFPQMLRDLRDAFSRVKTFFQTKDEV        EBV
SRGQYSREDNNCTHFPVGQSHMLLELRTAFSQVKTFFQTKDQL    moIL-10
SPGQGTQSENSCTHFPGNLPNMLRDLRDAFSRVKTFFQMKDQL    huIL-10
 KHKQSSFTKSC YPRGTLSQAVDALYIKAAWLKATIPEDRTK    huAK155

DNMLLDGSLLEDFKGYLGCQALSEMIQFYLEEVMPQAENHSTDQ   EHV
DNLLLKESLLEDFKGYLGCQALSEMIQFYLEEVMPQAENQDPE    EBV
DNILLTDSLMQDFKGYLGCQALSEMIQFYLVEVMPQAEKHGPE    moIL-10
DNLLLKESLLEDFKGYLGCQALSEMIQFYLEEVMPQAENQDPD    huIL-10
NIRLLKKKTKKQFM   KNCQFQEQLLSFFMEDVFGQLQLQG     huAK155

EKDKVNSLGEKLKTLRVRLRRCHRFLPCENK                EHV
AKDHVNSLGENLKTLRLRLRRCHRFLPCENK                EBV
IKEHLNSLGEKLKTLRMRLRRCHRFLPCENK                moIL-10
IKAHVNSLGENLKTLRLRLRRCHRFLPCENK                huIL-10
  CKKIRFVEDFHTLRQKLSHCIS    CASS               huAK155
```

TABLE 2-continued

Comparison of various IL-10 embodiments compared to AK155. First group is signal sequences, which are not aligned (Shown below are amino acid residues 1–18 of SEQ ID NO:3; 1–23 of SEQ ID NO:4; 1–18 of SEQ ID NO:5; 1–18 of SEQ ID NO:6; and 1–21 of SEQ ID NO:2, respectively).

| | |
|---|---|
| SKAVEQVKSAFSKLQEKGVYKAMSEFDIFINYIEAYMTTKMKN | EHV |
| SKAVEQIKNAFNKLQEKGIYKAMSEFDIFINYIEAYMTIKAR | EBV |
| SKAVEQVKSDFNKLQDQGVYKAMNEFDIFINCIEAYMMIKMKS | moIL-10 |
| SKAVEQVKNAFNKLQEKGIYKAMSEFDIFINYIEAYMTMKIRN | huIL-10 |
| AREMKSITRMKRTFYRIGNKGIYKAISELDILLSWIKKLLESSQ | huAK155 |

By Northern blot analysis, it is clear that AK155 is expressed in virus transformed T cell lines from primates, including humans. Reverse transcription polymerase chain reaction (RT PCR) has indicated that AK155 is also expressed in PHA-activated PBMC, and in Jurkat and Sup-Til cell lines. Hybridization to mRNA indicates expression in human kidney, and is detected in lung and liver tissue. The transcript size is about 1.0–1.2 kb, and the gene has been mapped to human chromosome 12q15. Transcripts for AK155 have not been detected by Northern analysis in PHA activated PBMC, Jurkat cells, owl monkey kidney (OMK) cells, and human herpes infected OMK cells, and by RT PCR analysis of HeLa cells, and the EBV-free B cell line BJA-B.

The structural homology of AK155 to the related IL-10 proteins suggests similar function of this molecule. AK155 likely mediates immune functions via a receptor of the class of cytokine receptors, possibly even sharing parts or all of the functional IL-10 receptor complex.

AK155 agonists (or antagonists), may also act as receptor agonists (or antagonists), which increase (or block) signaling via the AK155 receptor. Thus, AK155, or its agonistic or antagonist homologues, may be useful in the treatment of disorders of the immune system.

II. Purified AK155

Human AK155 amino acid sequence is shown in SEQ ID NO:2. This amino acid sequence can be used for providing sequence information in the cytokine allowing for distinguishing the protein antigen from other proteins and exemplifying numerous variants. Moreover, the peptide sequences allow preparation of peptides to generate antibodies to recognize such segments, and nucleotide sequences allow preparation of oligonucleotide probes, both of which are strategies for detection or isolation, e.g., cloning, of genes encoding such sequences.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, etc. Such fragments may have ends which begin and/or end at virtually all positions, e.g., beginning at residues 1, 2, 3, etc., and ending at, e.g., 150, 149, 148, etc., in all combinations. Particularly interesting peptides have ends corresponding to structural domain boundaries, e.g., helices A, B, C, or D. Note that the sequence of AK155 exhibits particular identity to cellular IL-10 in the region from residue 126–137.

The term "binding composition" refers to molecules that bind with specificity to AK155, e.g., in an antibody-antigen interaction. It also includes compounds, e.g., proteins, which specifically associate with AK155, including in a natural physiologically relevant protein-protein interaction, either covalent or non-covalent. Binding compositions also include molecules that specifically bind to AK155, when AK155 is bound to its receptor. The molecule may be a polymer, or chemical reagent. A functional analog may be a protein with structural modifications, or it may be a molecule which has a molecular shape which interacts with the appropriate binding determinants. The compounds may serve as agonists or antagonists of a receptor binding interaction.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. For diagnostic purposes, the temperature will usually be about room temperature or warmer, but less than the denaturation temperature of components in the assay. For therapeutic purposes, the temperature will usually be body temperature, typically about 37° C. for mammals, though under certain situations the temperature may be raised or lowered in situ or in vitro.

The solvent and electrolytes will usually be biologically compatible, and of a type that preserves biological activities. Usually the solvent will have a pH near neutral, that is, between pH 6.0 to pH 8.0. On some occasions, a detergent or surfactant will be added to maintain solubility of the AK155, AK155 variant or mutein, or anti-AK155 antibody. Where the protein is fully denatured, the protein can be maintained in solution, for example, by 1.0% sodium dodecyl sulfate (SDS) or by 16% Triton X-100. Where the protein is to be maintained in a non-denatured, biologically active state, the detergent may be Triton X-100, Tween 20, Brij 58, CHAPS, cholate, deoxycholate, or other detergents or stabilizers, as described, see, e.g., Weiner and Kotkoskie (2000) *Excipient Toxicity and Safety*, Marcel Dekker, Inc., New York, N.Y.; Sigma-Aldrich, Co. (2002) *Catalogue*, St. Louis, Mo.; U.S. Pat. No. 6,096,728 issued to Collins, et al.

III. Physical Variants

This invention also encompasses proteins or peptides having substantial amino acid sequence identity with the amino acid sequence of the AK155 antigen. The variants include species, polymorphic, or allelic variants.

The isolated AK155 DNA can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, antigenic, or other functional activity. These modified sequences can be used to produce mutant antigens or to enhance expression. Enhanced expression may involve gene amplification, increased transcription, increased translation, and other mechanisms.

The invention also contemplates new constructs that may be made from combining similar functional domains from other proteins. For example, target-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992.

IV. Functional Variants

The blocking of physiological response to AK155s may result from the competitive inhibition of binding of the ligand to its receptor. AK155 binding to IL-10 receptor may serve to induce signaling, e.g., send a signal similar to binding by IL-10. Alternatively, AK155 binding to IL-10 receptor may block IL-10 signaling. An AK155 antagonist would be expected to have the opposite effect as AK155.

In vitro assays of the present invention will often use isolated protein, soluble fragments comprising receptor binding segments of these proteins, or fragments attached to solid phase substrates. These assays will also allow for the diagnostic determination of the effects of either binding segment mutations and modifications, or cytokine mutations and modifications, e.g., AK155 analogues.

This invention also contemplates the use of competitive drug screening assays, e.g., where neutralizing antibodies to the cytokine, or receptor binding fragments compete with a test compound.

"Derivatives" of AK155 antigens include amino acid sequence mutants from naturally occurring forms, glycosylation variants, and covalent or aggregate conjugates with other chemical moieties. Covalent derivatives can be prepared by linkage of functionalities to groups which are found in AK155 amino acid side chains or at the N- or C-termini, e.g., by standard means. See, e.g., Lundblad and Noyes (1988) *Chemical Reagents for Protein Modification,* vols. 1–2, CRC Press, Inc., Boca Raton, Fla.; Hugli (1989) *Techniques in Protein Chemistry,* Academic Press, San Diego, Calif.; and Wong (1991) *Chemistry of Protein Conjugation and Cross Linking*, CRC Press, Boca Raton, Fla.

Fusion polypeptides between AK155s, its variants or muteins, and a fusion partner are provided. Many cytokine receptors or other surface proteins are multimeric, e.g., homodimeric entities, and a repeat construct may have various advantages, including lessened susceptibility to proteolytic cleavage. Typical examples of a fusion protein partner are a FLAG sequence, which allows ready detection by anti-FLAG antibody, a histidine tag, which allows purification by immobilized metal ions or by immobilized anti-$HIS_6$, and glutathione S-transferase, which constitutes a powerful technique for purification by immobilized glutathione. Other gene fusion protein partners include bacterial β-galactosidase, trpE, protein A, β-lactamase, alpha amylase, alcohol dehydrogenase, and yeast alpha mating factor (Sigma-Aldrich, Co. (2001) *Products for Life Science Research,* St. Louis, Mo.; pp. 45–89; Amersham Pharmacia Biotech (2001) *BioDirectory,* Piscataway, N.J., pp. 384–391). Recombinant techniques allow fusion to appropriate segments, e.g., to a FLAG sequence or an equivalent which can be fused via a protease-removable sequence (Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System,* Qiagen, Inc., Chatsworth, Calif.

Fusion peptides will typically be made by either recombinant nucleic acid methods or by synthetic polypeptide methods.

This invention also contemplates the use of derivatives of AK155 proteins other than variations in amino acid sequence or glycosylation. Such derivatives may involve covalent or aggregative association with chemical moieties or protein carriers. Covalent or aggregative derivatives will be useful as immunogens, as reagents in immunoassays, or in purification methods such as for affinity purification of binding partners, e.g., other antigens. An AK155 can be immobilized by covalent bonding to a solid support such as cyanogen bromide-activated Sepharose®, by methods which are well known in the art, or adsorbed onto polyolefin surfaces, with or without glutaraldehyde cross-linking, for use in the assay or purification of anti-AK155 antibodies or an alternative binding composition. The AK155 proteins can also be labeled with a detectable group, e.g., for use in diagnostic assays. Purification of AK155 may be effected by an immobilized antibody or complementary binding partner, e.g., binding portion of a receptor.

The present invention contemplates the isolation of additional closely related species variants. Southern and Northern blot analysis will establish that similar genetic entities exist in other mammals. It is likely that AK155s are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the molecules will be greatly accelerated by the isolation and characterization of additional distinct species or polymorphic variants of them. In particular, the present invention provides useful probes for identifying additional homologous genetic entities in different species.

The isolated genes will allow transformation of cells lacking expression of an AK155, e.g., either species types or cells which lack corresponding proteins and exhibit negative background activity. This should allow analysis of the function of AK155 in comparison to untransformed control cells.

Dissection of critical structural elements which effect the various physiological functions mediated through these antigens is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390.

Intracellular functions would probably involve receptor signaling. However, protein internalization may occur under certain circumstances, and interaction between intracellular components and cytokine may occur. Specific segments of interaction of AK155 with interacting components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Structural studies of the AK155 antigens will lead to design of new antigens, particularly analogs exhibiting agonist or antagonist properties on the molecule. This can be combined with previously described screening methods to isolate antigens exhibiting desired spectra of activities.

Chemical synthesis of peptides and chemical modification of existing peptides has been described (Merrifield (1963) *J. Amer. Chem. Soc.* 85:2149–2156; Merrifield (1986) *Science* 232: 341–347; Atherton, et al. (1989) *Solid Phase Peptide*

Synthesis: A Practical Approach, IRL Press, Oxford; Grant (1992) Synthetic Peptides: A User's Guide, W. H. Freeman, N.Y.; Hackeng, et al. (1999) Proc. Nat. Acad. Sci. USA 96:10068–10073; Stewart and Young (1984) Solid Phase Peptide Synthesis, Pierce Techniques in Protein Chemistry II, Academic Press, San Diego, Calif. Chemical Co., Rockford, Ill.; Bodanszky and Bodanszky (1984) The Practice of Peptide Synthesis, Springer-Verlag, N.Y.; Bodanszky (1984) The Principles of Peptide Synthesis, Springer-Verlag, N.Y.).

V. Antibodies

Antibodies can be raised to various epitopes of the AK155 proteins, including species, polymorphic, or allelic variants, and fragments thereof, both in their naturally occurring forms and in their recombinant forms. Additionally, antibodies can be raised to AK155s in either their active forms or in their inactive forms, including native or denatured versions. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective AK155s, or screened for agonistic or antagonistic activity, e.g., mediated through a receptor. Antibodies may be agonistic or antagonistic. An antagonistic antibody may act by steric blocking. These monoclonal antibodies will usually bind with at least a $K_D$ of about 1 mM, more usually at least about 300 $\mu$M, typically at least about 100 $\mu$M, more typically at least about 30 $\mu$M, preferably at least about 10 $\mu$M, and more preferably at least about 3 $\mu$M or better.

A solubilized AK155 or fragment of this invention can be used as an immunogen for the production of antisera or antibodies specific for binding. Purified antigen can be used to screen monoclonal antibodies or antigen-binding fragments, encompassing antigen binding fragments of natural antibodies, such as, Fab, Fab', and F(ab)$_2$. Purified AK155 antigens can also be used as a reagent to detect antibodies generated in response to the presence of elevated levels of the cytokine, which may be diagnostic of an abnormal or specific physiological or disease condition. This invention contemplates antibodies raised against amino acid sequences or fragments encoded by all or part of the nucleotide sequence of SEQ ID NO:1. In particular, this invention contemplates antibodies having binding affinity to or being raised against specific domains, e.g., as determined by a Parker antigenicity plot or Welling antigenicity plot, and the like, with use of software such as MacVector 6.5® (Accelrys, San Diego, Calif.).

Antibody to antigen binding properties can be measured by surface plasmon resonance (Karlsson, et al. (1991) J. Immunol. Methods 145:229–240; Neri, et al. (1997) Nat. Biotechnol. 15:1271–1275; Jonsson, et al. (1991) Biotechniques 11:620–627) or by competition ELISA (Friguet, et al. (1985) J. Immunol. Methods 77:305–319; Hubble (1997) Immunol. Today 18:305–306).

The antibodies of this invention can also be useful in diagnostic applications. As capture or non-neutralizing antibodies, they can be screened for ability to bind to the antigens without inhibiting binding to a receptor. As neutralizing antibodies, they can be useful in competitive binding assays. They will also be useful in detecting or quantifying AK155 protein or its receptors. See, e.g., Chan (ed.) (1987) Immunology: A Practical Guide, Academic Press, Orlando, Fla.; Price and Newman (eds.) (1991) Principles and Practice of Immunoassay, Stockton Press, N.Y.; and Ngo (ed.) (1988) Nonisotopic Immunoassay, Plenum Press, N.Y. Cross absorptions or other tests will identify antibodies which exhibit various spectra of specificities, e.g., unique or shared species specificities.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) Basic and Clinical Immunology (4th ed.), Lange Medical Publications, Los Altos, Calif., and references cited therein; Harlow and Lane (1988) Antibodies: A Laboratory Manual, CSH Press; Goding (1986) Monoclonal Antibodies: Principles and Practice (2d ed.), Academic Press, New York; and particularly in Kohler and Milstein (1975) in Nature 256:495–497, which discusses one method of generating monoclonal antibodies.

Production of antibodies without antigen isolation or purification is contemplated. Animals can be immunized with cells bearing the antigen of interest. Splenocytes can then be isolated from the immunized animals, and the splenocytes can fused with a myeloma cell line to produce a hybridoma (Meyaard, et al. (1997) Immunity 7:283–290). Resultant hybridomas can be screened for production of the desired antibody by means of functional assays or biological assays, that is, assays not dependent on possession of the purified antigen. In some cases, immunization with cells containing membrane-bound antigen may succeed in antibody generation, where immunization with purified antigen fails (Kaithamana, et al. (1999) J. Immunol. 163:5157–5164).

A variety of approaches are used to make therapeutic antibodies, or fragments thereof. Therapeutic antibodies include anti-ErbB-2 (Herceptin®) for treatment of breast cancer (Yip and Ward (2002) Cancer Immunol. Immunother. 50:569–587; U.S. Pat. No. 5,772,997 issued to Hudziak, et al.), anti-α-integrin chain (Antegren®) for treatment of multiple sclerosis (Brody (1997) Analyt. Biochem. 247:247–256; Lin and Castro (1998) Curr. Opinion Chem. Biol. 2:453–457), and anti-integrin $\alpha_v\beta3$ for inhibition of angiogenesis induced by tumors (Rader, et al. (1998) Proc. Natl. Acad. Sci. USA 95:8910–8915). Therapeutic antibodies also include anti-tumor necrosis factor-α for treatment of Crohn's disease (Targan, et al. (1997) New Engl. J. Med. 337:1029), anti-IL-1 for treatment of collagen-induced arthritis (Joosten, et al. (1996) Arthritis and Rheumatism 39:797), anti-1L-4 and anti-IL-5 for treatment of experimental asthma (Corry, et al. (1996) J. Exp. Med. 183:109), anti-IL-5 for human asthma (Leckie, et al. (2000) The Lancet 356:2144), anti-IL-8 for experimental reperfusion injury (Sekido, et al. (1993) Nature 365:654), anti-IL-10 for treatment of parasitic infections (King, et al. (1996) J. Immunol. 156:4715; Reiser and Stadecker (1996) New Engl. J. Med. 335:1369), anti-1L-18 for treatment of experimental arthritis (Joosten, et al. (2000) J. Immunol. 165:6553).

Therapeutic antibodies occurring as conjugated antibodies or fusion protein antibodies are contemplated. Antibodies conjugated to toxins, such as diptheria toxin, ricin, and Pseudomonas endotoxin are described (van Oosterhout, et al. (2001) Int. J. Pharm. 221:175–186; Marsh and Klinman (1990) 144:1046–1051; Kreitman (2001) Curr. Pharm. Biotechnol. 2:313–325; Dinndorf, et al. (2001) J. Immunother. 24:511–516). Antibodies are conjugated to small drug molecules, such as doxorubicin (Wahl, et al. (2001) Int. J. Cancer 93:540–600), calicheamicin (Garber (2000) J. Nat. Cancer Instit. 92:1462–1464), and dexamethasone (Everts, et al. (2002) J. Immunol. 168:883–889). Antibodies are conjugated to enzymes, where the enzyme is used to generate an active drug from a pro-drug (Chen, et al. (2001) *Int. J. Cancer* 94:850–858). Antibodies are conjugated to liposomes, e.g., for drug delivery (Shaik, et al. (2001) *J. Control. Release* 76:285–295; Park, et al. (2001) *J. Control. Release* 74:95–113). Conjugation of antibody to polyethylene glycol (PEG) may result in a prolongation of circulating time and a reduction of antigenicity (Trakas and Tzartos (2001) *J. Neurochem.* 120:42–49). Conjugation with PEG may be especially useful for therapeutic antibody fragments, such as Fab', Fv, and short chain Fv, which tend to have relatively short lifetimes in vivo (Chapman, et al. (1999) *Nature Biotechnology* 17:780–783). Antibody fusion proteins, such as an antibody fusion protein bearing a recognition tag, where the tag binds a toxin, are described (Gaidamakova, et al. (2001) *J. Control. Release* 74:341–347). Other antibody fusion proteins include, e.g., an engineered fusion protein comprising IgG and CD20 (Rituximab®) for treatment of non-Hodgkin's lymphoma (Coiffier, et al. (2002) *New Engl. J. Med.* 346:235–242).

Conjugated antibodies are useful for diagnostic or kit purposes, and include antibodies coupled to dyes, such as fluorescein or phycoerythrin, radioactive atoms, such as iodine-125, enzymes, such as horse radish peroxidase (Le Doussal, et al. (1991) *J. Immunol.* 146:169–175; Gibellini, et al. (1998) 160:3891–3898; Hsing and Bishop (1999) *J. Immunol.* 162:280414 2811), colloidal gold (Everts, et al. (2002) *J. Immunol.* 168:883–889), or various other moieties (Harlow and Lane (1988) *Antibodies A Laboratory Manual*, Cold Spring Harbor Laboratory, Cold Spring Harbor, N.Y.). Labeling of antibodies and proteins are taught, e.g., by U.S. Pat. Nos. 3,817,837; 3,850,752; 3,939,350; 3,996,345; 4,277,437; 4,275,149; and 4,366,241.

The binding of diagnostic antibodies to cells can be measured by immunochemistry or by flow cytometry (Everts, et al. (2002) *J. Immunol.* 168:883–889).

Humanized antibodies are contemplated. The use of non-human sources can limit the therapeutic efficiency of a monoclonal antibody. Antibodies derived from murine or other non-human sources can have the undesired properties of provoking an immune response, weak recruitment of effector function, and rapid clearance from the bloodstream (Baca, et al. (1997) *J. Biol. Chem.* 272:10678–10684). For these reasons, it may be desired to prepare therapeutic antibodies by humanization. A humanized antibody contains the amino acid sequences from six complementarity deteriming regions (CDRs) of the parent mouse antibody, which are grafted on a human antibody framework. To achieve optimal binding, the humanized antibody may need fine-tuning, by changing certain framework amino acids, usually involved in supporting the conformation of the CDRs, back to the corresponding amino acid found in the parent mouse antibody. An alternative to humanization is to use human antibody libraries displayed on phage (Vaughan, et al. (1996) *Nat. Biotechnol.* 14:309–314; Barbas (1995) *Nat. Med.* 1:837–839) or human antibody libraries contained in transgenic mice (Mendez, et al. (1997) *Nat. Genet.* 15:146–156).

The antibodies of this invention can also be used for affinity chromatography in isolating the protein. Columns can be prepared where the antibodies are linked to a solid support. See, e.g., Wilchek et al. (1984) *Meth. Enzymol.* 104:3–55.

Antibodies raised against each AK155 will also be useful to raise anti-idiotypic antibodies. These will be useful in detecting or diagnosing various immunological conditions related to expression of the respective antigens.

VI. Nucleic Acids

The described peptide sequences and the related reagents are useful in detecting, isolating, or identifying a DNA clone encoding AK155, e.g., from a natural source. Typically, it will be useful in isolating a gene from mammal, and similar procedures will be applied to isolate genes from other species, e.g., warm blooded animals, such as birds and mammals. Cross hybridization will allow isolation of AK155 from the same, e.g., polymorphic variants, or other species.

This invention contemplates use of isolated DNA or fragments to encode a biologically active corresponding AK155 polypeptide. In addition, this invention covers isolated or recombinant DNA which encodes a biologically active protein or polypeptide and which is capable of hybridizing under appropriate conditions with the DNA sequences described herein. Said biologically active protein or polypeptide can be an intact antigen, or fragment, and have an amino acid sequence disclosed in, e.g., SEQ ID NO:2. Further, this invention covers the use of isolated or recombinant DNA, or fragments thereof, which encode proteins which exhibit high identity to an AK155 or which was isolated using cDNA encoding an AK155 as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and/or flanking genomic sequences from the originating species. The term embraces a nucleic acid sequence which has been removed from its naturally occurring environment, and includes recombinant or cloned DNA isolates and chemically synthesized analogs.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, e.g., products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Recombinant engineering can be used to join together nucleic acid segments of desired functions to generate a single genetic entity comprising a desired combination of functions not found in the commonly available natural forms. Joining may be made to occur at naturally occurring restriction sites, at restriction sites artificially introduced by site-directed mutagenesis, or at restriction sites introduced by use of linkers or polylinkers.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides, e.g., 67, 73, 81, 89, 95, etc.

A DNA which codes for an AK155 protein will be particularly useful to identify genes, mRNA, and cDNA species which code for related or similar proteins, as well as DNAs which code for homologous proteins from different species. There are likely homologs in other species, including primates, rodents, canines, felines, and birds. Various AK155 proteins should be homologous and are encompassed herein. However, even proteins that have a more distant evolutionary relationship to the antigen can readily be isolated under appropriate conditions using these sequences if they are sufficiently homologous. Primate AK155 proteins are of particular interest.

Recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology*, Academic Press, San Diego, pp.1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach*, IRL Press, Oxford; and Rosenberg (1992) *J. Clinical Oncology* 10:180–199.

Substantial homology, e.g., identity, in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence of AK155, e.g., in SEQ ID NO:1 or 3. Typically, selective hybridization will occur when there is at least about 55% identity over a stretch of at least about 30 nucleotides, preferably at least about 75% over a stretch of about 25 nucleotides, and most preferably at least about 90% over about 20 nucleotides (See, e.g., Kanehisa (1984) *Nuc. Acids Res.* 12:203–213). The length of identity comparison, as described, may be over longer stretches, and in certain embodiments will be over a stretch of at least about 17 nucleotides, usually at least about 28 nucleotides, typically at least about 40 nucleotides, and preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., usually in excess of about 37° C., typically in excess of about 55° C., preferably in excess of about 70° C. Stringent salt conditions will ordinarily be less than about 1000 mM, usually less than about 400 mM, typically less than about 250 mM, preferably less than about 150 mM, including about 100, 50, or even 20 mM. However, the combination of parameters is much more important than the measure of any single parameter. See, e.g., Wetmur and Davidson (1968) *J. Mol. Biol.* 31:349–370.

AK155 from other mammalian species can be cloned and isolated by cross-species hybridization of closely related species. Homology may be relatively low between distantly related species, and thus hybridization of relatively closely related species is advisable. Alternatively, preparation of an antibody preparation which exhibits less species specificity may be useful in expression cloning approaches.

VII. Making AK155; Mimetics

DNA which encodes the AK155 or fragments thereof can be obtained by chemical synthesis, by screening cDNA or genomic libraries.

Chemical synthesis can be used for preparing polynucleotides of up to about 80 bases in length (Sambrok and Russell (2001) *Molecular Cloning*, $3^{rd}$ ed., Cold Spring Harbor Press, Cold Spring Harbor, N.Y., p.13.4). Variants and muteins of AK155 can be prepared by chemical mutagenesis or by recombinant mutagenic techniques. Recombinant mutagenic techniques include cassette mutagenesis (U.S. Pat. No. 5,747,038 issued to Presta, et al.), overlap extension mutagenesis (Horton, et al. (1993) *Methods in Enzymol.*, 217, Part H (ed. by R. Wu) Academic Press, San Diego, Calif., pp. 270–279; Sambrook and Russell (2001) *Molecular Cloning*, $3^{rd}$ ed., Cold Spring Harbor Laboratory Press, Cold Spring Harbor, N.Y., pp. 13.36–13.39), or megaprimer mutagenesis (Fieschi, et al. (1996) *Analyt. Biochem.* 234:210–214; Ling, et al. (1995) *Analyt. Biochem.* 230:167–172; Picard, et al. (1994) *Nucleic Acids Res.* 22:2587–2591).

Microarrays of nucleic acids may be used for screening (Ausubel, et al. (2001) *Curr. Protocols Mol. Biol.*, Vol. 4, John Wiley and Sons, New York, N.Y., pp. 22.0.1–22.3.26). For example, Huang, et al. (2000) described use of an array containing 1176-cancer-associated genes, including c-Myc, as applied in testing astrocytomas (Huang, et al. (2000) *Cancer Res* 60:6868–6874). Screening of cells and tissues is described, e.g., Ausubel, et al. (2001) *Curr. Protocols Mol. Biol.*, Vol. 4, John Wiley and Sons, New York, N.Y., pp. 25.0.1–25B.2.20 and Ausubel, et al. (2001) *Curr. Protocols Mol. Biol.*, Vol. 3, John Wiley and Sons, New York, N.Y., pp. 14.0.1–14.14.8.

DNA obtained by chemical means, screening, recombinant techniques, and combinations thereof, can be expressed in a wide variety of host cells for the synthesis of a full-length AK155 or fragments thereof.

Viral vectors suitable for the expression of genes in eukaryotic cells include alphaviruses, such as Sindbis virus, Simian virus, e.g., SV40, lentivirus, and baculovirus. Alphaviruses can infect a variety of cells, including kidney cells, neuronal cells, liver cells, fibroblasts, and dendritic cells. The life cycle of alphaviruses occurs in the cytoplasm, not the nucleus, and thus expression from these viruses does not depend on integration sites (Koller, et al. (2001) *Nature Biotechnology* 19:851). Whole animals and mammalian cells may be engineered by use of a virus. Adenovirus and coxsackie virus can be used to introduced genes into animals, where specific membrane-bound proteins serve as points of viral attachment (Kreda, et al., (2000) *Nature Biotechnology* 18:635; Bergelson, et al. (1997) *Science* 275:1320; Wickham, et al. (1993) *Cell* 73:309; Reynolds, et al. (2001) *Nature Biotechnology* 19:838). Sendai virus is used for the transfection of mammalian cells, where this virus binds to a receptor on the apical cell surface (Yonemitsu, et al. (2000) *Nature Biotechnology* 18:970; Hasan, et al. (1997) *J. Gen. Virol.* 78:2813). Lentivirusus can integrate their genomes into the chromosomes of non-dividing cells (Berkowitz, et al., (2001) *Virology* 279:116; Berkowitz, et al. (2001) *J. Virol.* 75:3371). Murine leukemia virus is used for transfer to a variety of human cells, including stem cells, T cells, fibroblasts, myoblasts, and hepatocytes (Cheng, et al. (1998) *Blood* 92:83). Transgenic animals can be prepared by techniques well known in the art (Eiges, et al. (2001) *Current Biology* 11:514).

Vectors suitable for expression in bacterial cells include pFLAG-ATS® (Sigma-Aldrich (2000) Products for Life Science Research, Sigma-Aldrich, St. Louis Mo.), pGEX-2T®, pEZZ 18® (Amersham Pharmacia (2001) BioDirectory, Amersham-Pharmacia, Piscataway, N.J.), pBR322 and pGEM-3Z® (Promega (2002) Life Science Catalog, Promega Corp., Madison, Wis.). Vectors suitable for expression in eukaryotic cells include pEFBOS (Henneke, et al. (2001) *J. Immunol.* 167:7069–7076), pBC1®, pGene/5-His®, Flp-In®, pIND-E®, pDisplay®, and pcDNA®, where the pcDNA® vectors are available with cytomegalovirus, hEF-1α, and UB promoters ((2001) Invitrogen 2001 Catalogue, Invitrogen Corp., Carlsbad, Calif.).

It will often be desired to express an AK155 polypeptide in a system which provides a specific or defined glycosylation pattern. See, e.g., Luckow and Summers (1988) *Bio/Technology* 6:47–55; and Kaufman (1990) *Meth. Enzymol.* 185:487–511.

The AK155, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

VIII. Uses

A. General.

The present invention provides reagents which will find use in diagnostic applications as described elsewhere herein, e.g., in AK155 mediated conditions, or below in the description of kits for diagnosis.

This invention also provides reagents with significant therapeutic potential. The AK155 (naturally occurring or recombinant), fragments thereof, and antibodies thereto, along with compounds identified as having binding affinity to AK155, should be useful in the treatment of conditions associated.

Conversely, antagonists of AK155, such as muteins or variants of a naturally occurring form of AK155 or blocking antibodies, may provide a selective and powerful way to block immune-related disease conditions.

AK155 antibodies or AK155 analogues, muteins, or antagonists, can be purified and then administered to animals or human patients. These reagents can be combined for therapeutic use with additional active or inert ingredients, e.g., in conventional pharmaceutically acceptable carriers or diluents, e.g., immunogenic adjuvants, along with physiologically innocuous stabilizers, excipients, or preservatives. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using AK155 or fragments thereof can be performed to identify compounds having binding affinity to or other relevant biological effects on AK155 functions, including isolation of associated components. Subsequent biological assays can then be utilized to determine if the compound has intrinsic stimulating activity and is therefore a blocker or antagonist in that it blocks the activity of the cytokine. Likewise, a compound having intrinsic stimulating activity can activate the signal pathway and is thus an agonist in that it simulates the activity of AK155. This invention further contemplates the therapeutic use of blocking antibodies to AK155 as antagonists and of stimulatory antibodies as agonists. This approach should be particularly useful with other AK155 species variants.

In addition, the cytokine appears to be expressed in kidney cell, and may play a role in that organ's function, e.g., ion exchange or blood pressure regulation. The cytokine may also have water balance functions. The cytokine may have some detectable expression in kidney.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Dosage levels and dosage schedules will reflect a number of factors, including, the in vivo concentrations that are physiologically effective, in vivo concentrations that produce toxicity, pharmacokinetics, e.g., lifetime in bloodstream, rate of turnover and excretion, chemical stability of the therapeutic agent during storage and administration, and availability of agents that increase the efficacy and stability of the contemplated therapeutic agent.

The patient's condition will be monitored in order to determine optimal levels of dosing or infusion, optimal frequency of dosing or infusion, and any need for administration of multiple therapeutic agents, including drugs, chemotherapy, and surgery. Patient monitoring will be by radiographic, fluorescent, ultrasound, computed tomography techniques. Patient monitoring will also include examination by high pressure liquid chromatography (HPLC) of plasma analytes, cytologic methods, immunohistological assays, RT-PCR assays, and by visual inspection. Adverse events, such as chills, fever, anaphylaxis, opportunistic infections, and cardiac dysfunction, may be used as a guide for dosage and frequency of therapy (Slamon, et al. (2001) *New Engl. J. Med.* 344:783–792). Optimal dosage may also be adjusted in light of data from white blood cell counts, platelet counts, tests for hepatic function (bilirubin), renal function (creatinine), nausea, vomiting, and tests for neuropathy (Schiller, et al. (2002) *New Engl. J. Med.* 346:92–98).

AK155, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, topical, or parenteral (including subcutaneous, intramuscular, intravenous and intradermal) administration. The formulations may conveniently be presented in unit dosage form and may be prepared by any methods well known in the art of pharmacy. See, e.g., Hardman, et al. (2001) *Goodman and Gilman's the Pharmacological Basis of Therapeutics*, McGraw-Hill, New York, N.Y.; and Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Dekker, New York; Lieberman, et al. (eds.) (1990) *Pharmaceutical Dosage Forms: Tablets*, Dekker, New York; and Lieberman, et al. (eds.) (1990) *Pharmaceutical Dosage Forms: Disperse Systems*, Dekker, New York. The therapy of this invention may be combined with or used in association with other agents, e.g., other types of IL-10s, or their respective antagonists.

Both the naturally occurring and the recombinant form of AK155 are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble AK155 as provided by this invention.

One method of drug screening utilizes eukaryotic or prokaryotic host cells which are stably transformed with recombinant DNA molecules expressing AK155. Cells may be isolated which express AK155. Such cells, either in viable or fixed form, can be used for standard binding partner binding assays. See also, Parce, et al., (1989) *Science* 246:243–247; and Owicki, et al. (1990) *Proc. Natl. Acad. Sci. USA* 87:4007–4011, which describe sensitive methods to detect cellular responses.

Assays for gene expression are generally sensitive to expression of mRNA or to polypeptide. Assays for mRNA expression can be used for screening for cells expressing AK155 or variants thereof, for screening for cells expressing AK155 receptor, or for screening for therapeutic agents that modulate AK155 activity or modulate AK155 receptor activity. mRNA levels may be measured by techniques using hybridization, such as Northern blotting or the molecular beacon technique (Liu, et al. (2002) *Analyt. Biochem.* 300:40–45), or techniques that combine reverse transcription and the polymerase chain reaction (RT-PCR) See, e.g., Huang, et al. (2000) *Cancer Res.* 60:6868–6874). PCR product can be measured by incorporated radiolabel, by electrophoresis followed by staining with a dye, such as ethidium bromide. Alternatively, PCR product can be measured during each cycle of the PCR reaction, e.g., by means of TaqMan® (PE Applied Biosystems, Foster City, Calif.) probes or by SYBR Green I® (Molecular Probes, Eugene, Oreg.) (Wittwer, et al. (1997) *Biotechniques* 22:130–138; Schmittgen, et al. (2000) *Analyt. Biochem.* 285:194–204). The TaqMan® technique, and similar techniques, rely on nuclease digestion of a probe, where digestion releases a fluorescing dye, where release results in an increase in fluorescence (Heid, et al. (1996) *Genome Res.* 6:989–994).

Rational drug design may also be based upon structural studies of the molecular shapes of the AK155 and other effectors or analogues. Effectors may be other proteins which mediate other functions in response to binding, or other proteins which normally interact with AK155, e.g., a receptor. One means for determining which sites interact with specific other proteins is a physical structure determination, e.g., x-ray crystallography or 2 dimensional NMR techniques. These will provide guidance as to which amino acid residues form molecular contact regions, as modeled, e.g., against cellular IL-10. For a detailed description of protein structural determination, see, e.g., Blundell and Johnson (1976) *Protein Crystallography*, Academic Press, New York.

B. Disease Conditions.

The invention is contemplated for use in the treatment of disease states such as inflammation, skin conditions, allergies, and cancer.

It is also contemplated to use the invention for the treatment and diagnosis of herpesvirus saimiri, and related viruses. Infection with herpesvirus saimiri results in expression of AK155 by the human genome (Knappe, et al. (2000) *J. Virol.* 764:3881–3887). Infection of humans with herpesvirus saimiri may prove fatal (Breshears, et al. (2001) *J. Comp. Pathol.* 125:25–33). Herpesvirus saimiri is used as an expression vector for human T cells, for use in gene therapy (Hiller, et al. (2000) *Virology* 278:445–455). It is contemplated to use the invention to increase the efficiency of this application of the virus.

i. Cancer, Tumors, and Angiogenesis.

The invention is contemplated to be useful for controlling cancer cells, tumors, and other proliferating cells. Cytokines can be used for the treatment of various tumors. IL-2 administration provokes an increase in number of T cells, B cells, and NK cells, where these cells have antitumor activity. IL-2 treatment may be successful in treating melanoma and renal cell carcinoma. Interferon-α treatment, which increases the cytotoxic effect of NK cells, can be used to treat melanoma, renal carcinoma, lymphomas, and hairy cell leukemia (Abbas, et al. (2000) *Cellular and Mol. Immunol.* $4^{th}$ ed., W. B. Saunders Co., New York, p. 400).

IL-12 treatment can inhibit tumor growth, metastasis, and angiogenesis. Eradication of metastasis is initiated by IL-12's induction of T cells. Inhibition of angiogenesis by IL-12 requires the participation of IFN-γ which, in turn, stimulates IP-10, a CXC chemokine. IP-10, in turn, induces T cells to inhibit angiogenesis (Perti, et al., *J. Immunol.* 166, 6944 (2001)). IL-10 can have an antitumor effect, where administration of IL-12 together with IL-10 can have an additive antitumor effect (Berman, et al., *J. Immunol.* 157, 231 (1996)). IL-10 has an antitumor effect in animal studies of mastocytoma, breast cancer, melanoma, prostate cancer, and colon carcinoma. It is interesting to note that treatment with the variant of IL-10 of Epstein-Barr virus does not have an anti-tumor effect, but instead has a pro-tumor effect (Moore, et al. (2001) *Annu. Rev. Immunol.* 19:683).

Interferon-α plus zidovudine (inhibits DNA replication) produces dramatic results in the treatment of adult T-cell leukemia-lymphoma (Gill, et al. (1995) *New Engl. J. Med.* 332:1744). IL-2 with IFN-α-2a produces a measurable response in patients with metastatic renal-cell carcinoma (Negrier, et al. (1998) *New Engl. J. Med.* 338:1272).

The above studies involve systemic administration of cytokines, while the following study shows a mode of highly localized cytokine treatment. The C—C chemokine family attracts monocytes and lymphocytes, while C—X—C chemokines attract neutrophils and lymphocytes. For example, RANTES, a C—C chemokine, attracts T cells, NK cells, monocytes, eosinophils, basophils, and dendritic cells. Use of chemokines in anti-cancer therapy is illustrated by a bifunctional protein composed of RANTES linked to an antibody recognizing a tumor-specific antigen (RANTES-antibody). The antibody domain targets the bifunctional protein to cancer cells, while the chemokine moiety attracts immune cells which destroy the targeted cancer cell (Challita-Eid, et al. (1998) *J. Immuol.* 161:3729).

ii. IqE-Dependent Disease.

The contemplated invention is expected to be useful for treating IgE-dependent disease conditions, such as asthma, anaphylaxis, and allergic rhinitis (Salvi and Babu (2000) *New Engl. J. Med.* 342:1292; (Teran (2000) *Immunol. Today* 21:235; Marone (1998) *Immunol. Today* 19:5; Corrigan (1999) *Clin. Exp. Immunol.* 116:1).

Asthma is characterized by three features: intermittent and reversible airway obstruction, airway hyperresponsiveness, and airway inflammation (Galli (1997) *J. Exp. Med.* 186:343). Asthma involves the following series of events. Inhaled allergens encounter dendritic cells (allergen presenting cells; APCs) that line the airway. The dendritic cells then migrate to lymph nodes, where they present antigen to T cells. Contact of the dendritic cells with the T cells activates the T cells, and once activated, the T cells produce IL-4 and IL-13 (which act on B cells to promote IgE production) and IL-5 (which recruits eosinophils) (Jaffar, et al. (1999) *J. Immunol.* 163:6283).

B cells reside in lymph nodes. Two signals are required to provoke B cells to secrete IgE: (1) IL-4 (or IL-13) contact with B cells; and (2) T cell contact with B cells. The occurrence of both of these signals provokes the B cells to produce IgE. The IgE, in turn, circulates in the blood, where it may bind Fc$\epsilon$R1 of mast cells and basophils, provoking the mast cells and basophils to release various inflammatory agents and toxins. Mast cells can produce IL-1, IL-2, IL-3, IL-4, IL-5, granulocyte-macrophage stimulating factor, IFN-$\gamma$, and TNF-$\alpha$, histamine, leukotrienes, and toxic oxygen. Histamine and leukotrienes can provoke smooth muscles to contract, resulting in airway obstruction. IL-5 can recruit eosinophils, and once recruited, the eosinophils may produce "major basic protein," a protein that can directly damage the airways (Plager, et a. (1999) *J. Biol. Chem.* 274:14464). The eosinophils produce leukotrienes, which can provoke the airways to contract.

"Recruitment" of eosinophils means provoking or inducing the migration of eosinophils to migrate from the bloodstream to other locations, such as the airway. Recruitment may involve activation of integrin on the eosinophil surface, where activation is provoked by various cytokines. These cytokines may include eotaxin, RANTES, macrophage inflammatory protein-1$\alpha$, and monocyte chemotactic protein 1 (Busse and Lemanske (2001) *New Engl. J. Med.* 344:350).

Environmental allergens initiate the pathway leading to the production of IgE by B cells. These allergens also are used for the cross-linking of IgE/Fc$\epsilon$RI complexes residing on the surface of mast cells, where the cross-linking results in mast cell activation. Asthma tends to occur in people who are hypersensitive to specific environmental allergens, such as dust mite allergen, cockroach allergen, pollen, and molds (Barnes (1999) *New Engl. J. Med.* 341:2006). In humans, IgE is the main or only type of immunoglobin (Ig) that mediates airway hypersensitivity (Galli (1997) *J. Exp. Med.* 186:343). In fact, there is a strong correlation between serum IgE levels and asthma. IgE is elevated in patients with bronchial asthma and allergic rhinitis (Zuberi, et al. (2000) *J. Immunol.* 164:2667). Mast cells express receptors (Fc$\epsilon$RI) that bind the constant region of IgE antibodies. Injections of recombinant antibodies against IgE have been used to treat asthma. Here, the anti-IgE binds to IgE in the body, and competitively prevents this IgE from binding to Fc receptors (Barnes (1999) *New Engl. J. Med.* 341:2006). Anti-IgE treatment in humans also can result in the down-regulation of Fc$\epsilon$RI, as determined by studies of basophils and other cells (Saini, et al. (1999) *J. Immunol.* 162:5624).

When a mast cell bearing bound IgE molecules encounters an antigen recognized by the bound IgE molecule, the antigen binds, resulting in the mast cell secreting histamine, proteases, prostaglandins, leukotrienes, toxic oxygen, and cytokines. In this situation, the allergen cross-links IgE molecules that are bound to Fc$\epsilon$RI, resulting in activation of the mast cell (Kita, et al. (1999) *J. Immunol.* 162: 6901).

The airways of asthma patients contain accumulations of mast cells, but also of T cells (Th2 type), eosinophils, basophils, and macrophages. Macrophages express Fc$\epsilon$RIIB (low affinity IgE receptor), where binding of IgE plus allergen can stimulate the macrophage to release prostaglandins, toxic oxygen, and cytokines (Ten, et al. (1999) *J. Immunol.* 163:3851).

IL-10 appears to modulate allergic diseases, such as asthma, since IL-10 can inhibit cytokine production by eosinophils, can inhibit cytokine production by mast cells, and can inhibit airway neutrophilia and eosinophilia induced by antigenic challenge (Moore, et al. (2001) *Annu. Rev. Immunol.* 19:683; Zuany-Amorim, et al. (1995) *J. Clin. Invest.* 95:2644; Stampfli, et al. (1999) *Am. J. Respir. Cell Mol. Biol.* 21:586).

iii. Inflammatory Diseases of the Gut.

The contemplated reagent is expected to be of use for the treatment of inflammatory diseases of the gut, such as inflammatory bowel disease, Crohn's disease (Beutler (2001) *Immunity* 15:5; Targan et al. (1997) *New Engl. J. Med.* 337:1029), colitis (Simpson, et al. (1998) *J. Exp. Med.* 187:1225), and celiac disease. IL-10 modulates inflammatory bowel disease, as IL-10-deficient mice exhibit this disease and administration of IL-10 can prevent it (Kuhn, et al. (1993) *Cell* 75:263; Moore, et al. (2001) *Annu. Rev. Immunol.* 19:683).

iv. Autoimmune Diseases.

The contemplated reagent is also expected to be of use for treatment of autoimmune diseases, such as multiple sclerosis, diabetes mellitus, systemic lupus erythematosus (SLE), Sjogren's syndrome, scleroderma, polymyositis, autoimmune thyroid disease, autoimmune gastritis and pernicious anemia, and autoimmune hepatitis (Bradley, et al. (1999) *J. Immunol.* 162:2511; Stott, et al. (1998) *J. Clin. Invest.* 102:938; Rose and Mackay (1998) *The Autoimmune Diseases*, 3$^{rd}$ $^{ed.}$, Academic Press, San Diego, Calif.).

SLE may be treated with anti-IL-10 (Ishida, et al. (1994) *J. Exp. Med.* 179:305; Llorente, et al. (1998) *J. Exp. Biol.* 181:839; Moore, et al. (2001) *Annu. Rev. Immunol.* 19:683; Llorente, et al. (2000) *Arthritis Rheum.* 43:1790). IL-10 appears to modulate systemic lupus erythematosus because of the high expression of IL-10 in this disease (Moore, et al. (2001) *Annu. Rev. Immunol.* 19:683).

v. Immune Disease of the Nervous System.

The invention is contemplated to be useful for the treatment of diseases of the central and peripheral nervous systems, such as multiple sclerosis, perivenous encephalomyelitis, acute necrotizing hemorrhagic leukoencephalomyelitis, Guillain-Barre Syndrome, demyelinating neuropathy, and the POEMS Syndrome. Neutralization of IL-10 increases the severity of experimental autoimmune encephalomyelitis (EAE), an animal model for multiple sclerosis, while IL-10 treatment may inhibit EAE (Crisi, et al. (1995) *Eur. J. Immunol.* 23:3035; Moore, et al. (2001) *Annu. Rev. Immunol.* 19:683). It is interesting to point out the correlation between infection with Epstein-Barr virus and multiple sclerosis (Wandinger, et al. (2000) *Neurology* 55:178), the production of a viral version of IL-10 by Epstein-Barr virus, and the array of similar and different effects of human IL-10 and viral IL-10 (Moore, et al. (2001) *Annu. Rev. Immunol.* 19:683).

vi. Inflammatory and Immune-Related Disease of the Skin.

The contemplated reagent is expected to be useful for the treatment of disease states of the skin such as psoriasis, systemic lupus erythematosus (Tsokos and Liossis (1999) *Immunol. Today* 20:119), vitiligo, dermatitis herpetiformis, alopecia, atopic eczema, and atopic dermatitis (Robert and Kupper (1999) *New Engl. J. Med.* 341:1817), as well as autoimmune skin diseases that are organ specific, such as pephigus vulgaris, bullous pemphigoid, and pemphigus foliaceus (Davidson and Diamond (2001) *New Engl. J. Med.* 345:340). The contemplated reagent is also expected to be useful for enhancing the healing of chronic ulcers. The expected use of the invention for treatment of skin conditions is supported by the presence of AK155 receptor in keratinocytes.

Psoriasis is a skin disease involving hyperproliferation of keratinocytes, and an influx of T cells, neutrophils, macrophages, and dendritic cells. These T cells include skin homing T cells, that is, T cells that had passed through the blood vessel wall and left the bloodstream to migrate to the skin. Keratinocytes and antigen presenting cells (APCs) in the skin activate the T cells, where the activated T cells secrete growth factors and cytokines which, in turn, provoke keratinocyte growth (Bos and De Rie, *Immunol. Today* 20, 40 (1999)). There is some thought that $CD4^+$ T cells help initiate skin lesions, while $CD8^+$ T Cells are responsible for the persistence of the lesions (Robert and Kupper (1999) *New Engl. J. Med.* 341:1817).

Psoriasis appears to be partly dependent on interferon-γ (IFN-γ). IFN-γ is produced by T cells, where it is produced by $CD4^+$ T cells, $CD8^+$ T cells (Szabo, et al. (1998) *J. Invest. Dermatol.* 111:1072), and mast cells (Ackermann, et al. (1999) *Br. J. Dermatol.* 140:624). Studies of keratinocytes have shown that T cells isolated from psoriatic lesions secrete large amounts of interferon-γ. The study also revealed that T cells promote keratinocyte proliferation by an IFN-γ dependent pathway (Hong, et al. (1999) *J. Immunol.* 162:7480).

Psoriasis may be dependent on IL-2, as revealed by the following three studies: (1) Treating human white blood cells with IL-2 produced psoriasis-like symptoms. The study involved biopsies of human skin, and human white blood cells treated with IL-2, where the human skin was transplanted on mice and the cells were injected in the mice. The study demonstrated that IL-2 treatment was required for the production of psoriatic skin (Wrone-Smith and Nickoloff (1996) *J. Clin. Inv.* 98:1878); (2) Treating human patients with a fusion protein consisting of diphtheria toxin (a poison) linked to IL-2, resulted in an improvement of the disease (Granstein, *J. Clin. Invest.* 98, 1695 (1996); Gottleib, et al. (1995) *Nature Medicine* 5:442); and (3) Cyclosporin treatment of psoriasis patients resulted in a decrease in the number of T cells (where these T cells bore an IL-2 receptor) and in an improvement of the disease (Gottlieb, et al. (1992) *J. Invest. Dermatol.* 98:302).

Psoriasis may be dependent on IL-12. A mouse model of psoriasis was produced by injecting T cells into mice. The T cells were genetically deficient in IFN-γ, thus enabling detection of IFN-γ-independent pathways of psoriasis. The T cell injection resulted in psoriasis. This mouse model of psoriasis resemble human psoriasis, as it resulted in down growths of epidermis into dermis, called "elongation of rete pegs." The disease was prevented by injections of anti-IL-12 (Hong, et al. (2001) *J. Immunol.* 166:4765).

Psoriasis may be dependent on CCL20. Studies of skin homing have revealed that keratinocytes produce a CC cytokine, CCL20 (macrophage inflammatory protein-3α). This cytokine binds to a receptor on T cells, called CCR6. Expression of both of these proteins is greatly elevated in psoriatic skin, as compared to normal skin (Homey, et al. (2001) *J. Immunol.* 164:6621).

Inflammatory skin diseases may be dependent on the chemokine CCL27 (CTACK). CCL27 is constitutively produced by keratinocytes, and can be induced by TNF-α and IL-1β. CCL27's receptor is CCR10. CCR10 occurs on T cells, as well a number of other cells (Homey, et al., *J. Immunol.* 164, 3465 (2000)). CCL27 is detected only in the skin, as revealed by studies of humans and mice (Morales, et al. (1999) *Proc. Natl. Acad. Sci. USA* 96:14470). CCL27 can attract a subset of T cells, namely, the $CLA^+$ memory T cells. Molecules used for the homing of T cells to the skin are discussed. About 90% of the T cells in inflammatory skin lesions express CLA, while under 5% of the T cells in non-skin inflamed sites express CLA. CLA is a membrane-bound protein that is a ligand for E-selectin (membrane-bound protein of epithelial cells of blood vessels). Interaction between CLA and E-selectin may be critical for recruiting T cells to sites of skin inflammation (Morales, et al. (1999) *Proc. Natl. Acad. Sci. USA* 96:14470). E-selectin is upregulated during inflammation (Tietz, et al. (1998) *J. Immunol.* 161:963). Another selectin, called P-selectin, also occurs on endothelial cells. T cells from psoriatic skin express ligands for both E- and P-selectin (Chu, et al. (1999) *J. Immunol.* 163:5086). Studies with mice demonstrated that E- and P-selectin have functions that are quite similar (Tietz, et al (1998) *J. Immunol.* 161:963).

In addition to CLA, another membrane-bound protein of the T cell is used in T cell homing to the skin. LFA-1 is a membrane-bound protein of T cells. LFA-1 is a member of the integrin family of proteins. For T cells to bind to endothelial cells of a blood vessel, LFA-1 must first be activated. Activation appears to be dependent on chemokine receptors on the surface of the T cell (Stein, et al. (2000) *J. Exp. Med.* 191:61). Once LFA-1 is activated, it binds to ICAM (ICAM is an extracellular protein on the vascular endothelium). Clinical studies have shown that antibodies to LFA-1 can be used to treat psoriasis (Weitz-Schmidt, et al. (2001) *Nature Medicine* 7:687; Granstein (2001) *New Engl. J. Med.* 345:284; Gottlieb, et al. (2000) *J. Am. Acad. Dermatol.* 42:428).

Psoriasis may be triggered by bacterial antigens (Granstein (1996) *J. Clin. Invest.* 98:1695; Robert and Kupper (1999) *New Engl. J. Med.* 341:1817; Chu, et al. (1999) *J. Immunol.* 163:5086). Bacterial products, such as lipopolysaccharides, can activate white blood cells through the Toll-like receptor family of proteins (TLRs). The activated white blood cells, in turn, can release cytokines that recruit $CLA^+$ T cells to the skin. Alternatively, bacterial products may bind to MHC II and consequently serve to activate T cells (Travers, et al. (1999) *J. Clin. Invest.* 104:1181). Where a bacterial product binds directly to MHC without intracellular processing, it is called a "superantigen."

It will be apparent from the above commentary that the contemplated invention may be used for treating inflammatory conditions by interfering with the action of IFN-γ, IL-2, IL-12, CCL27 (=CTACK), CCL20, T cell receptor, the Toll-like receptors, or T cell homing proteins, such as LFA-3.

vii. Immune-Related Diseases of Muscle.

The invention is expected to be useful for autoimmune diseases of the muscle, such as myasthenia gravis (Balasa and Sarvetnick (2000) *Immunol. Today* 21:19; Sempowski, et a. (2001) *J. Immunol.* 166:2808), Lambert-Eaton myasthenic syndrome, polymyositis, and idiopathic inflammatory myopathy (Rose and Mackay (1998) *The Autoimmune Diseases*, 3rd ed., Academic Press, San Diego, Calif.).

viii. Transplant-Related Immune Diseases.

The invention is contemplated to be of use for treatment of transplant rejection and graft versus host disease (GVHD) (Blazar, et al. (1997) *Immunol. Revs.* 157:79). Studies with animals revealed that administration of IL-10 increased survival of various grafts and reduced GVHD-associated lethality (Moore, et al. (2001) *Annu. Rev. Immunol.* 19:683). In mice, Epstein-Barr virus IL-10 can inhibit the rejection of transplanted organs (Qin, et al. (1996) *J. Immunol.* 156:2316–2323; Suzuki, et al. (1995) *J. Exp. Med.* 182:477–486).

ix. Systemic Inflammation.

The invention is contemplated to be useful for the treatment of systemic inflammatory response, as may occur in septicaemia, septic shock, severe trauma, burns, and reperfusion injury. IL-10 has a protective role in endotoxemia (Pajkrt, et al. (1997) *J. Immunol.* 158:3971), while IL-10-deficient mice have a dramatically increased susceptibility to lipopolysaccharide (Berg, et al. (1995) *J. Clin. Inv.* 96:2339; Moore, et al. (2001) *Annu. Rev. Immunol.* 19:683).

x. Infection.

It is contemplated to use the invention for the treatment of bacterial, fungal, and protozoal infections. A typical response to infections may involve recognition of the microbe or microbial products by macrophages, neutrophils, or dendritic cells. Macrophages may respond by producing various cytokines, i.e., IL-12, TNF, IL-1, and IL-18. The combination of IL-12, IL-1, and TNF, in turn, stimulates NK cells to produce interferon-γ (IFN-γ). IFN-γ, in turn, induces macrophages to produce toxic oxygen, to engage in phagocytosis, and induces infiltration by macrophages and neutrophils. IL-12 and IFN-γ provoke T cells to mount a further response to microbes (Moore, et al., *Annu. Rev. Immunol.* 19, 683 (2001)). Resistance to infection can be improved by reducing IL-10 levels, as shown by studies of IL-10-deficient mice and by treatment with anti-IL-10 (Dai, et al, *J. Immunol.* 158, 2259 (1997); Wagner, et al. (1994) *Infect. Immun.* 62:2345; Vazquez-Torres, et al. (1999) *Infect. Immun.* 67:670).

C. IL-8 and Inflammation.

IL-8 modulates psoriasis. IL-8 and IL-8 receptor (IL-8R) are both increased in psoriatic skin. Two types of IL-8 receptors have been found, CXCR1 and CXCR2 (Lippert, et al. (1998) *J. Immunol.* 161:2600–2608) IL-8 provokes an increase in proliferation and chemotaxis of keratinocytes (Michel, et al. (1997) *J. Immunol.* 159:6291–6297; Schutz, et al. (1993) *J. Immunol.* 151:4399–4406). Keratinocytes produce a number of cytokines, such as TNF-α, IL-1, IL-6, IL-8, and GM-CSF, where these cytokines may be responsible for provoking the infiltration of leukocytes (Ruckert, et al. (2000) *J. Immunol.* 165:2240–2250; Pei, et al., (1998) *J. Immunol.* 161:1954–1961). IL-8 is a potent attractant of neutrophils (Bruch-Gerharz, et a. (1996) *J. Exp. Med.* 184:2007–2012; Luster (1998) *New Engl. J. Med.* 338:436–445; Lippert, et al., (1998) *J. Immunol.* 161:2600–2608). Neutrophils can produce IL-8, and thus amplify inflammation by autocrine signaling (Kuhns, et al. (2001)) *J. Immunol.* 167:2869–2878). IL-8 may also be a mast cell attractant (Lippert, et al. (1998) *J. Immunol.* 161:2600–2608).

It is hypothesized to use antibodies to AK155 to modulate the expression of IL-8, to modulate IL-8-dependent activities such as migration or proliferation, and to modulate inflammation.

D. STAT3 and Inflammation.

Cytokines activate members of a family of cytoplasmic proteins called STAT. Cytokine signaling results in phosphorylation of STAT to produce STAT-phosphate (STAT-P) and in increased stability of STAT/STAT dimeric complexes (Stancato, et al. (1996) *J. Biol. Chem.* 271:4134–4137). Once activated, activated STAT translocates to the nucleus, where its binds to various promoters, resulting in changes in gene expression (Wong and Fish (1998) *J. Biol. Chem.* 273:309–314). For example, activation of T cells by RANTES and involves the activation of STAT1 and STAT3, with the consequent increase in expression of IL-2 receptor α-chain, IL-2, and IL-5 (Wong and Fish (1998) *J. Biol. Chem.* 273:309–314).

STAT3 may have different and even opposite functions, depending on the cell type and state of activation of the cell (Ahmed and Ivashkiv (2000) *J. Immunol.* 165:5227–5237). The following relates the effects of STAT3 in promoting or preventing activation of white blood cells. When IL-10 binds to the IL-10 receptor, STAT3 is recruited to the IL-10 receptor via tyrosine-P residues of the IL-10R1 subunit. IL-10R1 is one of the subunits of the IL-10 receptor (Moore, et al. *Ann. Rev. Immunol.* 19:683–765). Tyrosine kinases that are constitutively associated with the IL-10 receptor catalyze conversion of STAT3 to STAT3—P. STAT3 promotes survival of T cells and antibody production by B cells. In contrast, deletion of STAT3 results in activation of macrophages and promotion of inflammatory bowel disease (Ahmed and Ivashkiv (2000) *J. Immunol.* 165:5227–5237). Deletion of STAT3, where deletion is specifically in macrophages and neutrophils, results in activation of macrophages and neutrophils, impairment of IL-10 mediated functions, and inflammation of the gut (Takeda, et al. (1999) *Immunity* 10:39–49)). Other apparently opposite roles of STAT3 were found, where these roles related to increasing and suppressing apoptosis. Studies comparing normal mice with STAT3-knockout mice demonstrated that STAT3-deficiency increased apoptosis (and decreased proliferation) of T cells. However, other studies with normal mice and STAT3-knockout mice demonstrated that STAT3-deficiency suppressed apoptosis (and increased proliferation) of epithelial cells (Suzuki, et al. (2001) *J. Exp. Med.* 193:471–481).

It is hypothesized to use AK155 for the treatment of gut inflammation. The invention contemplates using AK155 for stimulating STAT3 phosphorylation in gut cells, for the enhancement of IL-10 function, and the reduction of gut inflammation.

E. Keratinocytes, ICAM-1, and Inflammation.

Interferon-γ modulates psoriasis. IFN-γ is produced by CD4$^+$ T cells, CD8$^+$ T cells (Szabo, et al. (1998) *J. Invest. Dermatol.* 111:1072), and mast cells (Ackermann, et al. (1999) *Br. J. Dermatol.* 140:624). T cells isolated from psoriatic lesions secrete large amounts of IFN-γ. T cells promote keratinocyte proliferation by an IFN-γ dependent pathway (Hong, et al. (1999) *J. Immunol.* 162:7480).

T cell activation plays a crucial role in the psoriatic lesion, as indicated by the success of various T cell-targeting drugs in the treatment of psoriasis (Bata-Csorgo, et al. (1995) *J. Invest. Dermatol.* 105:89S–94S). Interactions between LFA-1 of a T cell and ICAM-1 of a neighboring cell constitutes an interaction that mediates adhesion of the T cell to the neighboring cell as well as activation of the T cell (Dustin and Chan (2000) *Cell* 103:283–294; Weitz-Schmidt, et al. (2001) *Nature Medicine* 7:687–692). ICAM-1 is known as a counter-receptor of LFA-1. Inhibition of the LFA-1 to ICAM-1 interaction by antibodies against LFA-1, or by small molecules that bind LFA-1, can be used to treat psoriasis and other inflammatory diseases (Krueger, et al (2001) *J. Invest. Dermatol.* 115:333; Papp, et al. (2001) *J. Am. Acad. Dermatol.* 45:665–674; Weitz-Schmidt, et al. (2001) *Nature Medicine* 7:687–692). One example of an activating interaction between a T cell and a neighboring cell is that of a T cell and a keratinocyte. The keratinocyte can present antigen to a T cell via MHC Class II, where the MHC Class II serves to activate the T cell. The keratinocyte can also express ICAM-1, which serves as a co-activator of the T cells, where the ICAM-1 can bind to LFA-1 of the T cell (Nickoloff, et al. (1993) *J. Immunol.* 150:2148–2159). The result of the activating and co-activating interactions is activation of the T cell, an event in the mechanism of psoriasis.

Studies with mice genetically deficient in ICAM-1 demonstrated that lack of ICAM-1 can reduce migration of white blood cells to sites of inflammation. The ICAM-1 knock-out mice were studied on a wild-type background, as well as on a selectin minus background, i.e., mice doubly-deficient in ICAM-1 and selectin. Relief from some types of experimentally induced inflammation, such as experimental septic shock, was provided by the ICAM-1 deficiency alone, while relief from other types were provided by selectin deficiency alone, with maximal relief provided by deficiencies in both ICAM-1 and selectin (Steeber, et al. (1999) *J. Immunol.* 163:2176–2186).

It is hypothesized to use antibodies against AK155 for modulating the ability of ICAM-1 to serve as a receptor, and for treating inflammation.

ICAMs are a family of membrane-bound proteins. The ICAMs all bind to the integrin LFA-1 ($\equiv \alpha_L/\beta_2$ integrin), which is present on white blood cells, where ICAM-1 binds to an additional integrin Mac-1, and where ICAM-3 also binds $\alpha_D/\beta 2$ integrin (Kessel, et al. (1998) *J. Immunol.* 160:5579–5587). ICAM-1 is expressed at low levels under normal conditions and is up-regulated by cytokines on various white blood cells, endothelial cells, keratinocytes, and fibroblasts. ICAM-1 to LFA-1 interactions are used for adhesion of activated white blood cells to capillary epithelium, activation of helper T cells for the production of cytokines, and activation of cytotoxic T cells for killing infected cells. ICAM-2 is constitutively highly expressed by white blood cells. ICAM-3 is expressed by antigen presenting cells (APCs), while the other ICAMs may be low or absent on APCs (Holness, et al. (1995) *J. Biol. Chem.* 270:877–884; Edwards, et al. (1998) *J. Biol. Chem.* 273:28937–28944). Engagement of ICAM-3 provokes the secretion of IL-8, MIP-1α, or MCP-1 (Kessel, et al. (1998) *J. Immunol.* 160:5579–5587).

It is hypothesized to use AK155 to modulate the expression of an ICAM of a cell with a consequent change in T cell activation, in order to treat inflammation.

F. IL-10 and Inflammation.

An interrelationship between IL-10 and IL-8 may occur in psoriasis. IL-10 is an anti-inflammatory cytokine. Decreased expression of IL-10 receptor (IL-10R) may occur in psoriasis (Michel, et al. (1997) *J. Immunol.* 159:6291–6297). IL-8 has been found to down-regulate IL-10R (Michel, et al. (1997)). Hence, IL-8 can promote inflammation.

IL-10 has anti-inflammatory properties where the suppressive effect of IL-10 includes inhibition of secretion of inflammatory cytokines and inhibition of cell recruitment. Activated monocytes or macrophages secrete IL-1, IL-6, IL-12, IL-18, GM-CSF, and tumor necrosis factor, where this secretion is inhibited by IL-10 (Moore, et al., *Ann. Rev. Immunol.* 19:683–765). IL-10 also inhibits secretion of a number of cytokines involved in cell recruitment. CC chemokines, e.g., RANTES, and CXC chemokines, e.g., IL-8, are secreted by active monocytes, where this secretion is inhibited by IL-10. The CC chemokines and CXC chemokines recruit monocytes, dendritic cells, neutrophils, and T cells. Thus, IL-10 inhibits production of cytokines that are most closely with inflammation, such as IL-1 and tumor necrosis factor, and with cytokines most closely associated with chemotaxis, i.e., the chemokines (Moore, et al. *Ann. Rev. Immunol.* 19:683–765).

IL-10 inhibits the inflammation of inflammatory bowel disease (IBD), psoriasis, and other diseases. IL-10 inhibits IBD as shown by studies demonstrating that IL-10 knockout mice develop IBD (Kuhn, et al. (1993) *Cell* 75:263–274), and other studies showing that IL-10 treatment prevents experimental IBD (Groux and Powrie (1999) *Immunol. Today* 20:442–445). IL-10 also inhibits or suppresses inflammation of the skin (Berg, et al. (1995) *J. Exp. Med.* 182:99–108), where suppression inflammation may involve downregulation of ICAM-1 (Koppelman, et al. (1997) *Immunity* 7:861–871), CD80, and CD86 (Mitra, et al. (1995) *J. Immunol.* 154:2668–2677). ICAM, CD80, and CD86 are co-stimulatory molecules used for activating T cells. Specifically, CD80 and CD86 of an antigen presenting cell (APC) co-stimulates a T cell by binding to CD28 of the T cell (Lanier, et al. (1995) *J. Immunol.* 154:97–105). Where IL-10 downregulates ICAM-1, CD80, or CD86, its effect on the T cell is indirect. IL-10 also exerts a direct effect on a variety of cells of the immune system, including T cells, macrophages, and mast cells (Moore, et al. (1993) *Ann. Rev. Immunol.* 11:165–190). IL-10's direct effect on T cells may include suppressing the secretion of IL-2 and TNF-α (Groux and Powrie (1999) *Immunol. Today* 20:442–445).

It is hypothesized to use AK155 to modulate the expression of IL-10, where increased expression of IL-10 is expected to reduce inflammatory reactions.

G. B7-H1 and Inflammation. Activation of a T cell by an antigen presenting cell may involve interaction of the MHC/peptide complex (of the APC) with the T cell receptor (of the T cell) and interaction of B7-1 ($\equiv$CD80) or B-7-2 ($\equiv$CD86) (of the APC) with CD28 (of the T cell) (Mitra, et al. (1995) *J. Immunol.* 154:2668–2577). Studies using blocking antibodies have shown that in some situations signaling via B7-1 leads to a Th1-type response, while signaling via B7-2 leads to a Th2-type response (Elloso and Scott (1999) *J. Immunol.* 162:6708–6715). Administration of antibodies to B7-1 and B7-2 can prevent an immune response, e.g., rise in IgE after challenge with parasites (Greenwald, et a. (1997) *J. Immunol.* 158:4088–4096). B7-H1 has been identified as a member of the B7 protein family. Studies with purified T cells revealed that treatment with B7-H1 stimulated the secretion of IL-10, interferon-γ, but not of IL-2 or IL-4 (Dong, et al. (1999) *Nature Medicine* 5:1365–1369).

It is hypothesized to use the invention to modulate the expression of B7-H1, with consequent alterations in cell proliferation, cytokine synthesis, or inflammatory response.

H. Drugs; Anti-Inflammatory; Anti-Neoplastic. It is contemplated to use the invention in conjunction or combination with a therapeutic agent, such as an anti-inflammatory or an anti-neoplastic agent. Candidate anti-neoplastic agents include, and are not limited to, 5-fluorouracil, methotrexate, cis-platin, vinblastine, vincristine, 6 mercaptopurine, thioguanine, cytosine arabinoside, mechlorethamine, chlorambucil, melphalan oxazaphosphorines, carboplatin, spiroplatin, tetraplatin, doxorubicin, daunorubicin, etoposide, diethylstilbestrol, tamoxifen, and taxol (U.S. Pat. No. 6,066,668 issued Hausheer, et al.).

Candidate anti-inflammatory agents include, but are not limited to, corticosteroids, prodrug esters and pharmaceutically acceptable salts thereof including hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide (U.S. Pat. No. 6,294,170 issued to Boone, et al.).

Candidate anti-inflammatory drugs also include non-steroidal anti-inflammatory drugs (NSAID) (Hardman, et al. (2001) *Goodman and Gilman's the Pharmacological Basis of Therapeutics,* McGraw-Hill, New York, N.Y.). NSAIDs can be characterized into nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones. For example, such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate and sulfasalazine. Structurally related salicylic acid derivatives having similar analgesic and anti-inflammatory properties are also intended to be encompassed by this group (U.S. Pat. No. 6,096,728 issued to Collins, et al.).

IX. Kits

This invention contemplates use of AK155 polypeptides and nucleic acids, fragments thereof, and their fusion products in a variety of diagnostic kits and methods for detecting the presence of AK155, variants of AK155, or binding partners of AK155. Typically the kit will have a compartment containing either a defined AK155 peptide or gene segment or a reagent which recognizes one or the other, e.g., AK155 fragments or antibodies.

A kit for determining the binding affinity of a test compound to AK155 would typically comprise a test compound; a labeled compound, for example a binding partner or antibody having known binding affinity for AK155; a source of AK155 (naturally occurring or recombinant); and a means for separating bound from free labeled compound, such as a solid phase for immobilizing the molecule. Once compounds are screened, those having suitable binding affinity to the antigen can be evaluated in suitable biological assays, as are well known in the art, to determine whether they act as agonists or antagonists to the AK155 signaling pathway. The availability of recombinant AK155 polypeptides also provide well defined standards for calibrating such assays.

A preferred kit for determining the concentration of, e.g., an AK155 in a sample would typically comprise a labeled compound, e.g., binding partner or antibody, having known binding affinity for the antigen, a source of cytokine (naturally occurring or recombinant) and a means for separating the bound from free labeled compound, e.g., a solid phase for immobilizing the AK155. Compartments containing reagents, and instructions, will normally be provided.

Antibodies, including antigen binding fragments, specific for AK155 or fragments are useful in diagnostic applications to detect the presence of elevated levels of AK155 and/or its fragments. Such diagnostic assays can employ lysates, live cells, fixed cells or tissues, cell cultures, body fluids, and further can involve the detection of antigens related to the antigen in serum, or the like. Diagnostic assays may be homogeneous (without a separation step between free reagent and antigen-binding partner complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol.* 70:1–525; Harlow and Lane (1980) *Antibodies: A Laboratory Manual,* CSH Press, NY; and Coligan, et al. (eds.) (1997) *Current Protocols in Immunology,* Greene and Wiley, NY.

Anti-idiotypic antibodies may have similar use to diagnose presence of antibodies against an AK155, as such may be diagnostic of various abnormal states. For example, overproduction of AK155 may result in production of various immunological reactions which may be diagnostic of abnormal physiological states, particularly in proliferative cell conditions such as cancer or abnormal activation or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or binding partner, or labeled AK155 is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

There are also numerous methods of separating the bound from the free AK155, or alternatively the bound from the free test compound. The AK155 can be immobilized on various matrices followed by washing. Suitable matrices include plates, filters, plastic beads, magnetic beads (U.S. Pat. No. 6,342,588 issued to Osbourn, et al.; U.S. Pat. No. 6,340,569 issued to Ball, et al.; U.S. Pat. No. 6,329,159 issued to Andrew, et al.), and microfluidic devices (laboratory-on-a-chip) (U.S. Pat. No. 6,337,212 issued to Nagle, et a.; U.S. Pat. No. 6,132,685 issued to Kercso, et al.).

Diagnostic kits which also test for molecules other than AK155 and antibodies to AK155 are also contemplated, because a diagnosis may depend on the testing of multiple markers. Thus, kits may test for combinations of markers. See, e.g., Viallet, et al. (1989) *Progress in Growth Factor Res.* 1:89–97.

EXAMPLES

General Methods

Some of the standard methods are described or referenced, e.g., in Maniatis, et al. (1982) *Molecular Cloning, A Laboratory Manual,* Cold Spring Harbor Laboratory, Cold Spring Harbor Press; Sambrook and Russell (2001) *Molecular Cloning, 3rd. ed.,* Cold Spring Harbor Laboratory Press, Cold Spring Harbor, N.Y.; Wu (1993) *Recombinant DNA, Vol.* 217, Academic Press, San Diego, Calif.; Innis, et al. (eds.) (1990) *PCR Protocols: A Guide to Methods and Applications,* Academic Press, N.Y. Standard methods are also found in Ausbel, et al. (2001) *Current Protocols in Molecular Biology, Vols.*1–4, John Wiley and Sons, Inc. New York, N.Y., which describes cloning in bacterial cells and DNA mutagenesis (Vol.1), cloning in mammalian cells and yeast (Vol. 2), glycoconjugates and protein expression (Vol. 3), and bioinformatics (Vol. 4).

Methods for protein purification include such methods as ammonium sulfate fractionation, column chromatography, electrophoresis, centrifugation, crystallization, is described (Coligan, et al. (2000) *Current Protocols in Protein Science, Vol.* 1, John Wiley and Sons, Inc., New York). Chemical analysis, chemical modification, post-translational modification, and glycosylation of proteins is described (Coligan, et al. (2000) *Current Protocols in Protein Science, Vol.* 2, John Wiley and Sons, Inc., New York). The production, purification, and fragmentation of polyclonal and monoclonal antibodies has is described (Coligan, et al. (2001) *Current Protcols in Immunology, Vol.* 1, John Wiley and Sons, Inc., New York; Harlow and Lane (1999) *Using Antibodies,* Cold Spring Harbor Laboratory Press, Cold Spring Harbor, N.Y.).

Standard techniques for characterizing ligand/receptor interactions have been described (Coligan, et al. (2001) *Current Protcols in Immunology, Vol.* 4, John Wiley and Sons, Inc., New York).

In Cell culture techniques are described in Doyle, et al. (eds.) (1994) *Cell and Tissue Culture: Laboratory Procedures,* John Wiley and Sons, NY.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y. Fluorescent labeling of appropriate reagents was performed by standard methods.

Example 1

Cloning of Human AK155

AK155 was cloned from T cells transformed with herpesvirus saimiri. Expression of AK155 occurred with use of various strains of the virus, i.e., C488, A11, B-SMHI, and C488. The properties of human T lymphocytes transformed with herpesvirus saimiri have been described (Fickenscher, et al. (1996) *J. Virol.* 70:6012–6019; Knappe, et. al. (2000) 74:3881–3887).

AK155 gene was purified by subtractive hybridization, and eventually cloned and characterized. Reverse transcription-PCR indicated that AK155 is expressed in a variety of other cell types, including cells not virally transformed (Knappe, et al. (2000) *J. Virol.* 74:3881–3887).

AK155 cDNA can be used as a hybridization probe to screen a library from a desired source, e.g., a cDNA library prepared from a mammalian cell, normal tissue, or diseased tissue. It is contemplated to use AK155 cDNA for the detection, purification, and characterization of naturally occurring variants, e.g., mutants, allelic variants, and splice variants.

PBMC were prepared from a healthy human blood donor by conventional Ficoll gradients, as described, e.g., in Coligan, et al. *Current Protocols in Immunology* Greene/Wiley. Cells from this preparation were stimulated with PHA and cultivated in the presence of IL-2 for several weeks. See, e.g., Fickenscher and Fleckenstein, pp. 345–362, "Generation of human T cell lines using lymphotropic herpesviruses" in Adolph (ed) *Methods in Molecular Genetics: Molecular Virology Techniques Part A Vol.* 4, Academic Press, San Diego, Calif. RNA from these PHA-blasts was used later to subtract the normally occurring cDNAs.

Another portion of the PBMC preparation was infected with herpesvirus saimiri C488. See Fickenscher and Fleckenstein , pp. 345–362, above; and Biesinger, et al. (1992) *Proc. Natl. Acad. Sci. USA* 89:3116–3119. The infected cells were cultivated in the presence of IL-2 until growth transformation was established (several months). RNA was isolated from the transformed T cell line, designated 3C (see Fickenscher, et al. (1996) *The Immunologist* 4:41–43), after the cells had been stimulated using 1 ng/ml TPA (Fickenscher, et al.,(1996) *J. Virol.* 70:6012–6019) for four hours. RNA was isolated according to Chomczynski and Sacchi (1987) *Anal. Biochem.* 162:156–159. The subtractive cDNA library was prepared with a cDNA subtraction kit (from Clontech, Palo Alto, Calif.).

PCR products were cloned using a TA cloning kit (Invitrogen, Carlsbad, Calif.). The resulting cDNA plasmids were sequenced from both termini on an automated sequencer (Applied Biosystems, Foster City, Calif.).

Plasmid AK155 contains a cDNA fragment of 540 nt. There is a single large open reading frame found, starting at nucleotide 12, and ending at -nucleotide 524. Termination signals are not found in this partial cDNA. Using rapid amplification of cDNA ends (RACE), the remaining fragments of the entire cDNA were cloned. The transcript size is approximately 1.0 to 1.2 kb. Genomic structure analysis indicates that introns exist at or near to between nucleotides 206 and 207, of about 35 nucleotides; between 263 and 264, of about 60 nucleotides; between 398 and 399, of about 1.5 kb; and between 464 and 465, of about 86 nucleotides. The sequences of the short introns have been determined.

Example 2

Cellular Expression of Human AK155

Because of the sequence similarity to human IL-10, distribution was investigated for similar type cell types. A probe specific for cDNA encoding primate AK155 is labeled, e.g., by random priming.

AK155 is expressed in various T cell lines of human and non-human primates, which have been in-vitro transformed to stable IL-2 dependent growth by herpesvirus saimiri C488. This expression was analyzed by Northern blotting. Owl monkey kidney cells (OMK), which are a primate permissive system for the human virus, and virus-infected OMK, were negative by Northern blotting. TPA stimulation did not significantly increase AK155 transcript levels in virus-transformed T cells; and cyclosporin A did not inhibit its expression. Transcription has been confirmed by reverse transcription-polymerase chain reaction (RT-PCR) from transformed human T cells in 3C and CB15 cells (Biesinger, et al. (1992) *Proc. Natl. Acad. Sci. USA* 89:3116–3119; Fickenscher and Fleckenstein (1994); and Fickenscher, et al. (1996) *J. Virol.* 70:6012–6019). It is quite notable that AK155 is so strongly expressed in herpesvirus saimiri-transfomed T cells, which suggests a role in the transformation mechanism. Expression was also detected in a monkey T cell line 93C488, a cell line from Saguinus fuscicollis monkeys that produces virus particles.

By RT-PCR weak transcription was detected in human phytohaemagglutinin (PHA)-activated PBMC, and in T cell tumor lines like Jurkat (Schneider, et al (1977) *Int. J. Cancer* 19:621–626) and SupTil (ATCC CRL-1942; see (1986) *Science* 232:1123–1127; and (1984) *Cancer Res.* 44:5657–5660); and in HTLV-transformed human T cells MT2, C91 PL, and HUT102 (which do produce HTLV-Virions; see Popovic, et al., (1984) "Biology of Human T cell leukemia/lymphoma virus" in Klein (ed.) *Advances in Viral Oncology, Vol. 4*, Raven Press, N.Y.). Thus, a low level of AK155 expression seems typical for human T cells, e.g., leukemia cell lines (Jurkat etc.) and HTLV-transformed cells. Positive signal was detected in macrophages stimulated with interferon-γ (IFN-γ) or lipopolysaccharide (LPS), but not after treatment with Protein A expressing cells. No detectable signal was found in HeLa cells, BJA-B (human B-cell line which does not carry EBV genomes; see Klein, et al. (1974) *Proc. Natl Acad. Sci. USA* 71:3283–3286), Tera-2 (human teratocarcinoma cell line; ATCC HTB106 or CRL-1973), BCBL-1 (HHV8$^+$; an HHV8 virus, which is a close relative to H. saimiri, positive EBV negative human B cell line (Renne, et al. (1996) *Nature Medicine* 2:342–346), Kaposi's sarcoma (HHV8+; clinical sample), cervical carcinoma (HPVI6$^+$; clinical sample), thyroid, or kidney. The negative results from BJA-B and Tera-2 may suggest a possibility of specific expression in T cells and macrophages. The HHV8-infected cells like BCBL1 or the tumors did not express AK155, which means that it is therefore specific for H. saimiri. AK155 transcription was not seen in cervical carcinoma, which suggests that it does not play a significant role in at least one cancerous condition.

Using a commercial dot spot mRNA hybridization filter and standard hybridization conditions, faint expression was detected in human kidney, and even fainter in human lung and liver. By northern blot analysis, negative results were obtained from: PHA-activated peripheral blood mono-nuclear cells (PBMC), Jurkat, Owl monkey kidney cells (OMK; ATCC CRL 1556; Daniel, et al. (1976) *In Vitro* 12:290), and OMK infected with herpesvirus saimiri C488. By RT-PCR, Hela cells (epithelial; ATCC CCL-2.1: HeLa229; see (1985) *Am J. Pathol.* 119:361–366) and BJA-B (EBV-free B cell line; see Klein, et al. (1974) *Proc. Natl. Acad. Sci. USA* 71:3283–3286) gave undetectable expression. Dot blots gave undetectable signals in the following human tissues by mRNA dot spot assay: brain, amygdala, caudate nucleus, cerebellum, cerebral cortex, frontal lobe, hippocampus, medulla oblongata, occipital lobe, putamen, substantia nigra, temporal lobe, thalamus, subthalamic nucleus, spinal cord, heart, aorta, sceletal muscle, colon, bladder, uterus, prostate, stomach, testis, ovary, pancreas, pituitary gland, adrenal gland, thyroid gland, salivary gland, mammary gland, small intestine, spleen, thymus, peripheral leukocytes, lymph node, bone marrow, appendix, trachea, placenta, fetal brain, fetal heart, fetal kidney, fetal liver, fetal spleen, fetal thymus, fetal lung.

Example 3

Chromosome Mapping and Gene Structure of Human AK155

It was determined that an AK155 gene occurs human chrosome 12q15 region by comparison of the cloned AK155 sequence with high-throughput genomic sequence of human chromosome 12q15 made available in GenBank (accession no. AC007458; 191,111 bp; BAC RPCI11–444B24). Further comparison with appropriate genomic cosmids and plasmid subclones revealed the exon-intron structure of the AK155 gene. Five exons of 206, 57, 135, 66, and 583 bp are present, and these are disrupted by three small introns (85 bp, 159 bp, 86 bp) and one large intron (23 kb).

The predicted AK155 protein showed a 24.7% amino acid identity and 47% amino acid similarity to human IL-10 (Knappe, et al. (2000) *J. Virol.* 74:3881–3887).

Example 4

Purification of AK155 Protein

Multiple transfected cell lines are screened for one which expresses the cytokine at a high level compared with other cells. Various cell lines are screened and selected for their favorable properties in handling. Natural AK155 can be isolated from natural sources, or by expression from a transformed cell using an appropriate expression vector. Early results suggest that the cytokine, after secretion, rebinds to the cell surface. Purification of the expressed protein is achieved by standard procedures, or may be combined with engineered means for effective purification at high efficiency from cell lysates or supernatants. FLAG or His$_6$ segments can be used for such purification features. Alternatively, affinity chromatography may be used with specific antibodies, see below.

Example 5

AK155 Dimer Formation

AK155 was cloned in *E.coli*, using the vector pQE30 (Qiagen, Hilden, Germany), where the cloned protein had an N-terminal histidine tag. The cloned protein was purified under denaturing conditions and then exposed to renaturing conditions, i.e., dialysis. The dialyzed protein was then analyzed by sodium dodecylsulfate polyacrylamide electrophoresis (SDS PAGE) with or without heating with mercaptoethanol prior to loading on the gel. The dialyzed protein loaded as is migrated with a molecular weight of about 36 kDa. The dialyzed protein that was heat-treated in mercaptoethanol prior to loading migrated with a molecular weight of about 19 kDa. The higher apparent molecular weight of the non-heated protein indicated that the protein formed a dimer prior to loading, and maintained its dimeric state during electrophoresis.

The computed molecular weight, based on DNA sequence, of the AK155 polypeptide (monomer) is 19.8 kDa, which is consistent with that found where a heat-denatured AK155 was analyzed by SDS PAGE.

Further evidence for the dimeric state of AK155 was provided by analysis of AK155 extracted from mammalian cells. AK155 was cloned and expressed using the eukaryotic expression vector pME18S in COS-7 cells, where the protein was cloned with a FLAG sequence. The cells were extracted and the extracted protein was loaded as is, or heated with reductant, prior to loading on the electrophoresis gel. AK155 was not purified prior to analysis by SDS PAGE. Detection was by rabbit antiserum prepared against AK155 or by anti-FLAG monoclonal antibody. The results demonstrated an apparent molecular weight of about 19 kDa (with denaturation) and of about 36 kDa (without denaturation), again indicating formation of AK155 dimer (Knappe, et al. (2000) *J. Virol.* 74:3881–3887).

Example 6

Preparation of Antibodies Specific for AK155

Recombinant AK155 was prepared by cloning in *E.coli* using the pQE30® expression vector (Qiagen, Hilden, Germany). The expressed protein was purified using nickel-nitrilotriacetic acid-agarose, and used to raise polyclonal rabbit antisera. The anti-sera was used to detect the electrophoretic position of AK155 prepared after expression in *E. coli* using pQE30® or in COS-7 cells with expression by the eukaryotic expression vector pME18S (Knappe, et al. (2000) *J. Virol.* 74:3881–3887).

It is contemplated to raise antibodies against peptides derived from AK155 (Coligan, et al. (1994) *Current Protocols in Immunology* Vol. 2, Wiley and Sons, New York, N.Y., §§9.3–9.4). The use of free and unconjugated peptides for antibody generation is described, e.g., see Zhou and Whitaker (1993) *J. Immunol.* 150:1629–1642; Lenz, et al. (2001) *J. Immunol.* 167:1803–1808 (2001); Jiang, et al. (1995) *Oncogene* 10:1855–1864).

Analysis of SEQ ID NO:2 by MacVector 6.5® (Accelrys, San Diego, Calif.) indicated that the AK155 polypeptide sequence contained a number of regions predicted to have increased antigenicity. A Parker antigenicity plot revealed that regions approximately comprising amino acid residues 22–42, 53–65, 65–80, 110–134, and 145–153 are expected to have increased antigenicity. A Welling antigenicity plot showed that regions approximately comprising amino acid residues 15–28, 42–50, 64–75, and 110–118 are expected to have increased antigenicity. It is contemplated to use one or more of these antigenic regions, or a fragment of one or more of these antigenic regions, for antibody production. It is not intended to limit the invention to the use of the described regions and fragments for the production of antibodies.

Example 7

Evaluation of Breadth of Biological Functions

The native, recombinant, and fusion proteins would be tested for agonist and antagonist activity in many biological assay systems, e.g., on T cells, B cells, NK, macrophages, dentritic cells, hematopoietic progenitors, etc.

AK155 is evaluated for agonist or antagonist activity on transfected cells expressing IL-10 receptor and controls. See, e.g., Ho, et al. (1993) *Proc. Natl. Acad. Sci. USA* 90, 11267–11271; Ho, et a. (1995) *Mol. Cell. Biol.* 15:5043–5053;and Liu, et al. (1994). *J. Immunol.* 152:1821–1829.

Based, in part, upon the structural homology to IL-10, the AK155 is evaluated for effect in macrophage/dendritic cell activation and antigen presentation assays, T cell cytokine production and proliferation in response to antigen or allogeneic stimulus. See, e.g., de Waal Malefyt et al. (1991) *J. Exp. Med.* 174:1209–1220; de Waal Malefyt et al. (1991) *J. Exp. Med.* 174:915–924; Fiorentino, et al. (1991) *J. Immunol.* 147, 3815–3822; Fiorentino, et al. (1991) *J. Immunol.* 146:3444–3451; and Groux, et al. (1996) *J. Exp. Med.* 184:19–29.

AK155 will also be evaluated for effects on NK cell stimulation. Assays may be based, e.g., on Hsu, et al. (1992) *Internat. Immunol.* 4:563–569; and Schwarz, et al. (1994) *J. Immunother.* 16:95–104.

B cell growth and differentiation effects will be analysed, e.g., by the methodology described, e.g., in Defrance, et al. (1992). *J. Exp. Med.* 175:671–682; Rousset, et al (1992) *Proc. Natl. Acad. Sci. USA* 89:1890–1893; including IgG2 and IgA2 switch factor assays. Note that, unlike COS7 supernatants, NIH3T3 and COP supernatants apparently do not interfere with human B cell assays.

Example 8

Cloning α- and β-Subunits of the AK155 Receptor

The experiments described in this example demonstrate methods that may be used for cloning both the α- and β-subunits of the AK155 receptor. The experiments also describe methods by which cells that already express the β-subunit of the AK155 receptor (IL-10Rβ; IL-10R2) are transfected with the α-subunit of the AK155 receptor subunit (IL-20Rα; IL-20R1), and finally, the experiments reported in this example demonstrate how the AK155 receptor is expressed in a cell following cloning and transfection.

The α-subunit of the AK155 receptor was cloned into any one of a number of preferred vectors for expression (Balbas and Bolivar (1990) *Methods in Enzymology* 185:14–37). Vectors used for expression of genes in mammalian cells include pME-X, pCD-SRα, pCD, and pDNA1. Typically these vectors contain a promoter such as that is active in mammalian cells, stop and poyadenylation signals, and a drug-selection marker such as neomycin-resistance. In addition these vectors contain antibiotic resistance genes and an origin of replication for propagation in bacteria (Okayama and Berg (1985) *Mol. Cell Biol.* 5:1136–1142).

Cells were transfected using liposomes that were complexed with expression vectors for an AK155 α-subunit (FLAG-tagged CPNM1; CPNM1-FLAG) and an AK155 β-subunit (IL-10Rβ). Cells were cultured in DME with 5% fetal calf serum (FCS) until semiconfluent. Fugene 6® (Roche Molecular Biochemicals, Indianapolis, Ind., Cat. No.1814443) was diluted ⅟₄₀ in DME without serum and added dropwise to plasmid DNA in DME without serum at a ratio of 2 µl undiluted Fugene 6® per 1 g DNA. Plasmid/lipid solution was incubated for 15 min at room temperature and added dropwise to cells after changing media to DME serum.

Alternatively, Ba/F3 cells, a murine B cell line (Palacios and Steinmetz (1985) *Cell* 41:727–734), which also expresses a β-subunit of the AK155 receptor, were infected with retrovirus containing FLAG-CPNM1 (AK155 α-subunit) using retronectin-mediated infection. In certain cases, the cells were also transfected with retrovirus containing an AK155 β-subunit (hIL-10Rβ). Briefly, 60 mm petri dishes were coated with 2 ml of a 30–40 µg/ml dilution of retronectin (Takara, Tokyo, Japan, Cat. No. T100b) in water for 2 hrs at room temperature. Subsequently, the retronectin solution was removed and the petri dishes blocked with PBS with 2% bovine serum albumin (BSA) for 30 minutes at room temperature. Plates were washed with culture medium and cells (100,000) were applied. After 10 minutes, retrovirus containing supernatant harvested from packaging cells was added (Kitamura (1998) *Int. J. Hema-* tol. 67:351, Kitamura (2000) *Methods Mol. Biol.* 134:143, Kitamura (1995) *Proc. Natl. Acad. Sci. USA* 92:9146). The expression of the CPNM1-FLAG subunit was monitored using a biotinylated anti-FLAG (Sigma-Aldrich, St. Louis, Mo.) monoclonal antibody followed by Streptavidin-PE. Streptavidin-PE Cells were analyzed by fluorescence-activated-cell-sorting (FACS) and positive cells were sorted. An anti-hIL-20Rβ monoclonal antibody was used to monitor the expression of hIL-20Rβ.

Example 9

Analysis of Expression of Expression Using Quantitative Polymerase Chain Reaction (PCR)

This example demonstrates how the expression of chemokines, chemokine receptors and cell surface molecules is analyzed using quantitative PCR.

Colo-205 (American Type Culture Collection, Manassas, Va.; ATCC Cat. No. CCL222) cells (1.5–2 million/condition) were cultured overnight in RPMI-1640 without serum, and then treated with 250–300 ng of AK155 at 37° C. for 20 min to overnight, where the time of exposure depended on the gene to be assayed. After induction, cells were washed with phosphate buffered saline (PBS). RNA was isolated from cells by guanidinium isothiocyanate homogenization followed by ethanol precipitation using RNeasy Mini Kits® according to the manufacturers instructions (Qiagen, Valencia, Calif.). Total RNA (1 µg) was converted into cDNA using Superscript II® RNA H-reverse transcriptase (Gibco BRL, Rockville, Md.) according to manufacturers instructions, with the addition of 1 µM hexamers (Promega, Madison, Wis.).

cDNA (50 ng) was analyzed for the expression of cytokine, chemokine or chemokine receptor genes by the fluorogenic 5'-nuclease PCR assay (Holland et al. (1991) *Proc. Natl. Acad. Sci. USA* 88:7276–7280) using a Perkin-Elmer ABI Prism 7700 Sequence Detection System (ABI-PE, Foster City, Calif.). Reactions were incubated for 2 minutes at 50° C., denatured for 10 minutes at 95° C. and subjected to 40 two step amplification cycles with annealing/extension at 60° C. for 1 minute followed by denaturation at 95° C. for 15 sec. The reaction master mix was prepared according to the manufacturer's protocols to yield final concentrations of 1× PCR buffer, 200 µM dATP, dCTP, dGTP and 400 µM dUTP, 4 mM MgCl$_2$, 1.25 units of AmpliTaq DNA polymerase, 0.5 units of Amp-Erase® uracil-N-glycocylase (Perkin Elmer, Foster City, Calif.), 900 nM of each primer, and 250 nM probe.

The following primers and probes were used to detect the induction of IL-8, IL-10, ICAM-1, ICAM-2 and B7-H1:

| | | |
|---|---|---|
| (IL-8 forward) | TGGCAGCCTTCCTGATTTCT | (SEQ ID NO:7) |
| (IL-8 reverse) | TGCACTGACATCTAAGTTCTTTAGCA | (SEQ ID NO:8) |
| (IL-8 probe) | TGGCAAAACTGCACCTTCACACAGAGCT | (SEQ ID NO:9) |
| (IL-8 forward) | GAGATCTCCGAGATGCCTTCA | (SEQ ID NO:10) |
| (IL-8 reverse) | CAAGGACTCCTTTAACAACAAGTTGT | (SEQ ID NO:11) |
| (IL-10 probe) | TGAAGACTTTCTTTCAAATGAAGGATCAGCTGG | (SEQ ID NO:12) |
| (ICAM-1 forward) | GCCAGGAGACACTGCAGACA | (SEQ ID NO:13) |
| (ICAM-1 reverse) | TGGCTTCGTCAGAATCACGTT | (SEQ ID NO:14) |
| (ICAM-1 probe) | TGACCATCTACAGCTTTCCGGCGC | (SEQ ID NO:15) |
| (ICAM-2 forward) | CGGGAAGCAGGAGTCAATGA | (SEQ ID NO:16) |
| (ICAM-2 reverse) | GGGTTGCAGTGTCAGGATGA | (SEQ ID NO:17) |
| (ICAM-2 probe) | TCAGCGTGTACCAGCCTCCAAGGC | (SEQ ID NO:18) |
| (B7-H1 forward) | GGTGAATTGGTCATCCCAGAAC | (SEQ ID NO:19) |
| (B7-H1 reverse) | GATGGCTCCCAGAATTACCAAG | (SEQ ID NO:20) |
| (B7-H1 probe) | TCTGGCACATCCTCCAAATGAAAGGACTC | (SEQ ID NO:21) |

Amplicons were analyzed with 6-carboxy-fluorescein (FAM) labeled probes. Cytokine amplicons spanned at least one intron/exon boundary. A 18S rRNA amplicon was analyzed with a VIC® (Perkin Elmer, Foster City, Calif.) labeled probe under primer limiting conditions and used as an internal control for quantitation of the total amount of cDNA in a multiplex reaction. Concentrations of 18S rRNA probe, forward and reverse primers were 50 nM.

AK155 up-regulated the expression of IL-8, IL-10, ICAM-1, ICAM-2 and B7-H1 in Colo-205 cells, as determined by analysis of mRNA. Thus, AK155 binding to a AK155 receptor complex mediates the expression of several pro-inflammatory cytokines. Separate studies of colo-205 cells, involving analysis by flow cytometry, revealed that AK155 (10 ng/ml; 24 h) resulted in measurable cell surface expression of ICAM-1.

Example 10

AK155 Induces the Binding of STAT3 to Interferon-γ-Activated Sequences

AK155 induces DNA binding of STAT3 to IFN-γ-activated-sequences (GAS) in Ba/F3 cell lines (Murine B cell line, Palacios and Steinmetz (1985) *Cell* 41:727–734) transfected with the α-subunit of the AK155 receptor.

A. Preparation of Nuclear Extracts.

Mouse Pre-B cells, i.e., Ba/F3, transfected with AK155 α-subunit (CPNM1) and AK155 β-subunit (IL-10Rβ) were used for electrophoretic mobility shift assays (EMSA). Nuclear extracts were prepared after stimulation of cells with AK155.

Ba/F3 transfected cells (1.5–2 million/condition) cultured overnight in RPMI-1640 without serum were treated with 250–300 ng of AK155 at 37° C. for 20 min. Cells were washed with cold PBS and resuspended in Buffer A (basic phosphate buffer: 50 mM HEPES, 100 mM NaF, 10 mM Na$_4$PPi, 2 mM Na$_3$VO$_4$, 4 mM EDTA, 2 mM sodium molybdate and protease inhibitors (Complete Mini EDTA-Free protease inhibitor tablets; Boehringer-Mannaheim Cat. No.1836170) along with 10 mM MgCl$_2$ and 0.2% NP40) and incubated on ice for 1 min. After centrifugation at 2000 rpm for 1 min, cells were resuspended in Buffer B (Basic phosphate buffer with protease inhibitors, 10 mM MgCl$_2$ and 0.25M sucrose). Lysates were centrifuged at 2000 rpm for 1 min and the supernatant was aspirated. 100 μl of buffer C (Basic phosphate buffer with protease inhibitors and NP40) was added and the mixture was agitated at 4° C. for 30 min. Nuclear extracts were obtained as the supernatant after centrifugation of the lysate at 15,000 rpm for 30 min at 4° C.

B. DNA Binding Assays.

Nuclear or total cellular extracts were used for DNA binding analysis. Lysates (2–3 μl) were incubated with 51 μl 2× binding buffer (20 mM Tris HCl pH 8, 200 mM KCl, 10 mM MgCl$_2$ and 20% glycerol: 7 μl of 7.5% BSA, 4 μl 1 M dithiothreitol (DTT) and 20 μl 10% NP40 2× binding buffer before use), 1 μγl of poly dIdC (1 mg/ml) (Roche, Indianapolis, Ind.; Cat No. 1219847001) and 1 μl γATP end labeled annealed probe (the probe was gamma-activated sequence (GAS) at 10 fmol) for 30 min at room temperature. Samples were resolved on a 6% acrylamide gel in 0.25× TBE buffer at 150V. Gels were dried and exposed to film.

The results indicated that AK155 induced DNA binding by STAT3 to gamma-interferon-activated-sequences (GAS) in Ba/F3 cells treated with AK155.

Example 11

AK155 Stimulates Phosphorylation of STAT3

AK155 stimulates phosphorylation of STAT3 in Colo-205 cells. Colo-205 colon carcinoma cells (ATCC No. CCL222) were treated with prokaryotic recombinant histidine-tagged (His-AK155) or in some cases with glutathione S-transferase-tagged AK155 (GST-AK155). The phosphorylation of STAT3 was then determined by phospho-STAT3-specific Western blotting.

A. Treating Colo-205 Cell Line with AK155.

Cellular extracts of Colo-205 cells were prepared to analyze phosphorylation of STAT3 after Colo-205 cells were treated with AK155. Colo-205 cells (1.5–2 million/condition) were cultured overnight in RPMI-1640 without serum, treated with prokaryotic recombinant His-AK155 (10 ng/ml) for 5, 10, 20, 30, and 60 seconds. After induction, cells were washed with phosphate buffered saline (PBS) containing protease inhibitor cocktail tablets (Complete Mini EDTA-Free, Boehringer-Mannheim Cat. No.1836170). Total cellular lysis was carried out using a Brij lysis buffer (10 mM Tris pH 7.5, 2 mM EDTA, 0.15 M NaCl, 0.875% Brij 96 and 0.125% Nonidet P40) with protease inhibitors at 4° C. Cell lysates were clarified by centrifugation at 12,000 rpm for 15 min.

B. Electrophoresis of AK155 Induced Colo-205 Cell Extracts.

Samples were prepared for SDS-PAGE analysis by adding an equal volume of sample buffer (Novex, San Diego, Calif.; Cat. No. LC2676) and heating the mixture for 5 min in a boiling water bath. Aliquots of 10–15 μg were loaded on a 10% Tris-Glycine gel (Novex, San Diego, Calif.) and transferred to polyvinylidene difluoride (PVDF) membranes (Novex, San Diego, Calif.; Cat. No. LC 2002).

C. Immunoblotting for STAT3.

After transfer, membranes were incubated in blocking solution containing 3% skim milk in Tris buffered saline solution plus Tween (TBST; 10 mM Tris-HCl pH 8.0, 0.150 mM NaCl, 0.05% Tween 20) at room temperature for 30 min. Incubation with the primary antibody, anti-phospho-STAT3 (New England Biolabs, Beverly, Mass.; Cat. No.9131) was carried out overnight at 4° C. at a dilution of 1:1000. Membranes were washed in TBST and incubated with an anti-rabbit-horse radish peroxidase (HRP) conjugated secondary antibody at room temperature for 2–3 hours. HRP activity was detected using an Extended Signal® chemiluminescence kit (Pierce, Rockford, Ill.; Cat. No. CA47514) according to the manufacturer's recommendations. Total STAT3 in these samples was detected using a monoclonal antibody to STAT3 (BD Transduction Labs, Lexington, Ky.; Cat No. 21320).

D. Results.

Table 1 below illustrates the results of western blot analysis. AKI 155 treatment for five minutes as sufficient for induction of detectable levels of STAT3 phosphorylation. A lysate of the herpes virus samari-transformed T-cell line GB-i 5 served as a positive control (Table 1). Herpes virus samurai transformed T-cells secrete large amounts of AK155 (Knappe et al. (2000) *J. Virol.* 74:3881–3887) and constitutively ph sphorylate STAT3.

Table 1. Colo-205 cells treated with HIS-AK155 (10 ng/ml final concentration).

TABLE 1

Colo-205 cells treated with HIS-AK155 (10 ng/ml final concentration).

|  | 0 min | 5 min | 10 min | 20 min | 30 min | 60 min | CB-15 lysate |
|---|---|---|---|---|---|---|---|
| Phosphorylated STAT3 | --- | +++ | +++ | ++++ | ++++ | ++++ | ++ |

Table 2 below illustrates the results of western blot analysis demonstrating the dependence on AK155 concentration for inducing STAT3 phosphorylation in colo-205 cells. The results demonstrate that no signal was detected with 0.3 ng/ml, while approximately 1 ng/ml was sufficient to induce detectable levels of STAT3 phosphorylation.

Table 2. Colo-205 cells treated with His-AK155 (ng/ml final)

TABLE 2

Colo-205 cells treated with His-AK155 (ng/ml final)

|  | 0.0 ng/ml | 0.3 ng/ml | 1.0 ng/ml | 3.0 ng/ml | 10 ng/ml | 30 ng/ml | CB-15 lysate |
|---|---|---|---|---|---|---|---|
| Phosphorylated STAT3 | --- | --- | ++ | +++ | ++++ | +++ | ++ |

Table 3 below shows the results of western blot analysis where incubations were conducted in the presence and absence of antiserum to AK155. Western blot analysis demonstrated that rabbit anti-AK155 antiserum (10%) reduced the STAT3 phosphorylation signal. The results demonstrate that the high signal resulting from incubations with HIS-AK155 was largely prevented where incubations with HIS-AK155 also contained antiserum.

TABLE 3

Western blot analysis of the inhibition of STAT3 phosphorylation by anti-AK155 antiserum.

|  | CB-15 lysate | His-AK155 | HIS-AK155 + Antiserum | antiserum |
|---|---|---|---|---|
| Phosphorylated STAT3 | +++++++ | +++++++ | +/− | -------- |

Table 4 below illustrates the results of western blot analysis which showed that 1 U/ml heparin was sufficient to block STAT3 phosphorylation in Colo-205 cells.

TABLE 4

Colo-205 cells treated with HIS-AK155 (2 ng/ml final).

|  | 0.0 units heparin | 1 units heparin | 10 units heparin | 50 units heparin | 100 units heparin | 200 units heparin | CB-15 lysate |
|---|---|---|---|---|---|---|---|
| Phosphorylated STAT3 | +++ | --- | --- | --- | --- | --- | +++ |

In summary, the experiments reported in this example show that incubation of Colo-205 cells with HIS-tagged AK155 induced phosphorylation of STAT3 and that the induced phosphorylation can be prevented by antiserum against AK155.

AK155 was supplied as prokaryotic recombinant HIS-AK155 (10 ng/ml).

Example 12

AK155 Binds to Heparin

Herpes virus saimiri (HVS)-transformed T cells is a cell line that can secrete AK155. The influence of heparin (20 U/ml: 100 ug/ml) on the AK155 concentration in the culture supernatant was investigated. Supernatants (20 μl) and immunoprecipitates from 10 ml were analyzed by western blotting with rabbit anti-AK155 antiserum. After immunoprecipitation from supernatnats of HVS-transformed T cells, strong signals were detectable only in the presence of heparin. Thus, the addition of heparin to the T cell culture medium displaced AK155 from cell-surface glycoaminoglycans.

Supernatant (50 ml) from a HVS-transformed human T cell line, CB-15, was loaded on a heparin column (1 ml bed volume). The column was eluted with buffer containing 2 M salt. The first fractions to elute with the high-salt wash contained AK155, as shown by western blot analysis.

Example 13

Screening of Cell Lines that Respond to AK155, Correlation with Expression of α- and β-Subunits of the AK155 Receptor, and Screening of Different Sources of AK155

Cells which respond to AK155 treatment are those that express both the α- and β-subunits of the AK155 receptor.

A series of cell lines in addition to Colo-205 (Table 5) were tested for AK155 responsiveness. Responsiveness was evaluated by measuring AK155 induced STAT3 phosphorylation as described above.

The human cell lines SW403 (A; colon carcinoma), Lovo (B; colon carcinoma), and HaCaT (C; keratinocytes, known to react on IL-20) responded to AK155 treatment with STAT3 phosphorylation (Table 5). Phosphorylation could be blocked by heparin and by a rabbit antiserum against AK155 indicating that the specificity for AK155. Control experiments intended to detect the sum of non-phosphorylated and phosphorylated STAT3 demonstrated signals that were fairly constant, with western blot analysis of the various cell lines.

Table 5 shows that the following cell lines appear not to respond to treatment with AK155: HepG2 (hepatoma, IL-22 sensitive), Colo-320 (colon carcinoma), Molt-4 (lymphoma, IL-10 sensitive), Panc-I (pancreatic carcinoma), HeLa (cervical cancer), and 293T (transformed embryonic kidney cells). The following cell lines did show some constitutive phosphorylation of STAT3: HepG2, Panc-I, HeLa and 293T.

Remarkably, the supernatant from the HVS-transformed T-cell line CB-84 induced STAT3 phosphorylation in HepG2 cells. As noted above, HepG2 cells are not normally stimulated by AK155. The cell lines A495 (lung carcinoma, IL-22 reactive), KMH-2 (Hodgkin's disease), and human umbilical vein endothelial cells (HUVEC) did not react on AK155 treatment (data not shown).

A variety of cell types was tested by RT-PCR for the transcription of members of the cytokine receptor type 2 family (IL-10R1, IL-10Rβ, IL-20R1), IL-20R2, IL-22R, and GAPDH as a positive control). Dendritic cells (DC, differentiated in vitro from monocytes), LPS-activated monocytes, SW-403 (colon carcinoma), Lovo (colon carcinoma), HepG2 (hepatoma), Colo-320 (colon carcinoma), Colo-205 (colon carcinoma), HeLa (cervical carcinoma), KMH-2 (Hodgkin's disease). Panc-1 (pancreatic carcinoma), and HaCaT (keratinocytes). The responsiveness of cells to AK155 correlated with the expression of both the α-subunit and β-subunit of AK155 receptor. Where both of these subunits were not present, phosphorylation of STAT3 was not observed.

In addition to His-AK155, different preparations of AK155 were used: GST-AK155 (GST clipped off by protease treatment), AK155 purified from the Origami E. coli strain, and AK155 partially purified from the periplasm. His-AK155 had the strongest effects.

TABLE 5

Phosphorylation of STAT3 in various cell types in response to treatment with AK155.

| Cell type | STAT3 phosphoylation in response to AK155. | Transcription of the α-subunit of AK155 receptor (CPNM1). | Transcription of the β-subunit of AK155 receptor (IL-10R2). |
|---|---|---|---|
| Colo-205 (colon carcinoma) | +++ | +++ | +++ |
| HepG2 (hepatatoma, IL22-sensitive) | ---- | ---- | +++ |
| Colo-320 (colon carcinoma) | ---- | ---- | +++ |
| Molt-4 (lymphoma, IL-10 sensitive) | ---- | not tested | not tested |
| Panc-1 (pancreatic carcinoma) | ---- | ---- | +++ |
| HeLa (cervical cancer) | ---- | ---- | +++ |
| 293T (transformed embryonic kidney) | ---- | not tested | not tested |
| A495 (lung carcinoma, IL-22 reactive) | ---- | not tested | not tested |

TABLE 5-continued

Phosphorylation of STAT3 in various cell types in response to treatment with AK155.

| Cell type | STAT3 phosphoylation in response to AK155. | Transcription of the α-subunit of AK155 receptor (CPNM1). | Transcription of the β-subunit of AK155 receptor (IL-10R2). |
|---|---|---|---|
| KMH-2 (Hodgkin's Disease) | ---- | ---- | +++ |
| SW-403 (colon carcinoma) | +++ | +++ | +++ |
| Lovo (colon carcinoma) | +++ | +++ | +++ |
| HaCaT (keratinocytes, IL-20 reactive) | +++ | +++ | +++ |

Example 14

AK155 Induces the Expression of IL-8 and IL-10

AK155 induces the secretion of IL-8 from cultured cells (HaCaT, Lovo, colo-205). Incubation of HaCaT with without AK155 produced IL-8 at about 450 pg/ml, while AK155 (10 ng/ml) produced IL-8 at a level of 2500 pg/ml. Thus, a dramatic 5-fold increase in IL-8 concentration resulted with AK155-treatment. Incubation of Lovo cells without AK155 produced IL-8 at a level of about 30 pg/ml, while incubations with AK155 (10 ng/ml) produced 95 pg/ml IL-8. Table 6 shows that AK155 (2 ng/ml) treatment of colo-205 cells induces IL-8 and IL-10 production.

TABLE 6

Stimulation of expression of IL-8 and IL-10 in colo-205 cells by AK155.

| (pg/ml) | 24 h | | 48 h | |
|---|---|---|---|---|
| | without AK155 | with AK155 | without AK155 | with AK155 |
| IL-8 | 552 | 670 | 623 | 989 |
| IL-10 | 61 | 112 | 60 | 94 |

Colo-205 cells (ATCC No. CCL222) (1.5–2.0 million/test) were cultured overnight in RPMI-1640 without serum, and aliquoted into cell culture dishes at a density of $5 \times 10^5$ per well. Cells were then treated with 200 ng AK155 at 37° C. for 24 h. For samples to which anti-IL-10Rβ antibody was added, the anti-IL-10Rβ antibody was added at a concentration of 10 μg/ml at 0.5 h before the addition of AK155. After AK155 treatment, with or without antibody, the supernatant was collected and analyzed.

Immulon I® plates were coated with anti-IL-8 antibody (Endogen, Woburn, Mass.; Cat. No. M-801) in phosphate buffered saline at 4 μg/ml at 50 μl/well. Coated plates were incubated overnight at 4° C. or at 37° C. for 2 h. Non-specific binding was blocked with a blocking buffer, and the plates were incubated at room temperature for an additional hour. Blocking buffer is PBS with 20% fetal calf serum. Plates were washed with PBS containing 0.05% Tween-20. Standards and samples were added (at 50 μl/well) in duplicates and incubated at 37° C. After two hours plates were washed and an anti-IL-8 biotinylated antibody (Endogen, Woburn, Mass.; Cat No. M-802B) at a final concentration of 2 μg/ml (50 μl/well) in conjugate buffer was added. Conjugate buffer is blocking buffer with 0.05% Tween 20. Following an incubation of another hour at room temperature, a streptavidin-HRP linked antibody (Biosource, Hopkinton, Mass.; Cat. No. SNN204), at a final dilution of 1:25,000 (50 μl/well) was added (100 μl/well) to develop the ELISA, and the plates were read at 405 nm (Abrams (1995) Curr. Protocols Immunol. 13:61).

The effects of blocking antibodies was studied. When anti-IL-10Rβ antibody was added to the colo-205 cell culture 0.5 h before addition of AK155, the induction of IL-8 was blocked. The antibody against IL-10Rβ was called clone 90220, R&D. However, antibody to IL-10Rα did not influence the STAT3 phosphorylation. The antibody against IL-10Rα was called 3F9. Control studies demonstrated that equal amounts of STAT3 protein were present, by reprobing with antibody recognizing both non-phosphorylated and phosphorylated forms of STAT3.

Many modifications and variations of this invention, as will be apparent to one of ordinary skill in the art can be made to adapt to a particular situation, material, composition of matter, process, process step or steps, to preserve the objective, spirit, and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of the equivalents to which such claims are entitled; and the invention is not to be limited by the specific embodiments that have been presented herein by way of example.

What is claimed is:

1. An isolated antibody or binding fragment thereof which specifically binds to a polypeptide consisting of SEQ ID NO: 2 or an amino acid fragment thereof, wherein the amino acid fragment is at least 8 amino acids in length.

2. The antibody or binding fragment thereof of claim 1, wherein the binding fragment is an Fab fragment.

3. The antibody or binding fragment thereof of claim 1, wherein the binding fragment is an Fab' fragment.

4. The antibody or binding fragment thereof of claim 1, wherein the binding fragment is an F(ab)$_2$ fragment.

5. The antibody or binding fragment thereof of claim 1, wherein the binding fragment is an Fv fragment.

6. The antibody or binding fragment thereof of claim 1, wherein the binding fragment is a single chain antibody.

7. The antibody of claim 1, wherein the antibody is a polyclonal antibody.

8. The antibody of claim 1, wherein the antibody is a monoclonal antibody.

9. The antibody of claim 1, wherein the antibody is a humanized antibody.

10. The antibody of claim 1, wherein the antibody is a chimeric antibody.

11. The antibody or binding fragment of claim 1, which is detectably labeled.

12. The antibody of claim 1, wherein the amino acid fragment is at least 12 amino acids in length.

13. The antibody of claim 1, wherein the amino acid fragment is at least 16 amino acids in length.

14. The antibody of claim 1, wherein the amino acid fragment is at least 20 amino acids in length.

15. The antibody of claim 1, wherein the amino acid fragment consists of residues 16–39 of SEQ ID NO: 2.

16. The antibody of claim 1, wherein the amino acid fragment consists of residues 125–150 of SEQ ID NO: 2.

17. The antibody of claim 1, wherein the amino acid fragment consists of residues 22–171 of SEQ ID NO: 2.

* * * * *

UNITED STATES PATENT AND TRADEMARK OFFICE
CERTIFICATE OF CORRECTION

PATENT NO. : 6,797,813 B2  
APPLICATION NO. : 10/083720  
DATED : September 28, 2004  
INVENTOR(S) : Rene de Waal Malefyt et al.

Page 1 of 1

It is certified that error appears in the above-identified patent and that said Letters Patent is hereby corrected as shown below:

Title page: item

Item (*) should read

-- Notice: Subject to any disclaimer, the term of this patent is extended or adjusted under 35 U.S.C. 154(b) by 318 days. --

Signed and Sealed this

Tenth Day of March, 2009

JOHN DOLL  
*Acting Director of the United States Patent and Trademark Office*

SEQUENCE LISTING

<160> NUMBER OF SEQ ID NOS: 21

<210> SEQ ID NO 1
<211> LENGTH: 1076
<212> TYPE: DNA
<213> ORGANISM: Homo sapiens
<220> FEATURE:
<221> NAME/KEY: CDS
<222> LOCATION: (36)..(548)
<223> OTHER INFORMATION:

<400> SEQUENCE: 1

```
ctgtgagtga cacacgctga gtggggtgaa gggaa atg ctg gtg aat ttc att      53
                                        Met Leu Val Asn Phe Ile
                                        1               5 ttg agg tgt ggg ttg ctg tta gtc act ctg tct ctt gcc att gcc aag     101
Leu Arg Cys Gly Leu Leu Leu Val Thr Leu Ser Leu Ala Ile Ala Lys
            10                  15                  20 cac aag caa tct tcc ttc acc aaa agt tgt tac cca agg gga aca ttg     149
His Lys Gln Ser Ser Phe Thr Lys Ser Cys Tyr Pro Arg Gly Thr Leu
        25                  30                  35 tcc caa gct gtt gac gct ctc tat atc aaa gca gca tgg ctc aaa gca     197
Ser Gln Ala Val Asp Ala Leu Tyr Ile Lys Ala Ala Trp Leu Lys Ala
    40                  45                  50 acg att cca gaa gac cgc ata aaa aat ata cga tta tta aaa aag aaa     245
Thr Ile Pro Glu Asp Arg Ile Lys Asn Ile Arg Leu Leu Lys Lys Lys
55                  60                  65                  70 aca aaa aag cag ttt atg aaa aac tgt caa ttt caa gaa cag ctt ctg     293
Thr Lys Lys Gln Phe Met Lys Asn Cys Gln Phe Gln Glu Gln Leu Leu
                75                  80                  85 tcc ttc ttc atg gaa gac gtt ttt ggt caa ctg caa ttg caa ggc tgc     341
Ser Phe Phe Met Glu Asp Val Phe Gly Gln Leu Gln Leu Gln Gly Cys
            90                  95                  100 aag aaa ata cgc ttt gtg gag gac ttt cat agc ctt agg cag aaa ttg     389
Lys Lys Ile Arg Phe Val Glu Asp Phe His Ser Leu Arg Gln Lys Leu
        105                 110                 115 agc cac tgt att tcc tgt gct tca tca gct aga gag atg aaa tcc att     437
Ser His Cys Ile Ser Cys Ala Ser Ser Ala Arg Glu Met Lys Ser Ile
    120                 125                 130 acc agg atg aaa aga ata ttt tat agg att gga aac aaa gga atc tac     485
Thr Arg Met Lys Arg Ile Phe Tyr Arg Ile Gly Asn Lys Gly Ile Tyr
135                 140                 145                 150 aaa gcc atc agt gaa ctg gat att ctt ctt tcc tgg att aaa aaa tta     533
Lys Ala Ile Ser Glu Leu Asp Ile Leu Leu Ser Trp Ile Lys Lys Leu
                155                 160                 165 ttg gaa agc agt cag taaaccaaag ccaagtacat tgattttaca gttattttga    588
Leu Glu Ser Ser Gln
                170 aatacaataa gaactgctag aaatatgttt ataacagtct atttctttta aaaactttt    648 aacataatac tgacggcatg ttaggtgatt cagaatagac aagaaggatt tagtaaatta   708 acgttttgga tataagttgt cactaatttg cacattttct gtgttttcaa ataatgtttc   768 cattctgaac atgttttgtc attcacaagt acattgtgtc aacttaattt aaagtatgta   828 acctgaatta actcgtgtaa tatttgtgtg tggagtggga tgtgggggt ggaggggggaa   888 tgacagattt ctggaatgca atgtaatgtt actgagactt aaatagatgt tatgtatatg   948 attgtctgtt taagtgtttg aaaattgtta attatgccca gtgtgaactt agtacttaac  1008 acattttgat tttaattaaa taaattgggt ttccttctca aaaaaaaaaa aaaaaaaaa   1068 aaaaaaaa                                                          1076
```

<210> SEQ ID NO 2
<211> LENGTH: 171
<212> TYPE: PRT
<213> ORGANISM: Homo sapiens

<400> SEQUENCE: 2

```
Met Leu Val Asn Phe Ile Leu Arg Cys Gly Leu Leu Leu Val Thr Leu
1               5                   10                  15
```

```
Ser Leu Ala Ile Ala Lys His Lys Gln Ser Ser Phe Thr Lys Ser Cys
            20                  25                  30

Tyr Pro Arg Gly Thr Leu Ser Gln Ala Val Asp Ala Leu Tyr Ile Lys
        35                  40                  45

Ala Ala Trp Leu Lys Ala Thr Ile Pro Glu Asp Arg Ile Lys Asn Ile
 50                  55                  60

Arg Leu Lys Lys Lys Thr Lys Gln Phe Met Lys Asn Cys Gln
 65                  70                  75                  80

Phe Gln Glu Gln Leu Leu Ser Phe Phe Met Glu Asp Val Phe Gly Gln
                85                  90                  95

Leu Gln Leu Gln Gly Cys Lys Lys Ile Arg Phe Val Glu Asp Phe His
            100                 105                 110

Ser Leu Arg Gln Lys Leu Ser His Cys Ile Ser Cys Ala Ser Ser Ala
            115                 120                 125

Arg Glu Met Lys Ser Ile Thr Arg Met Lys Arg Ile Phe Tyr Arg Ile
        130                 135                 140

Gly Asn Lys Gly Ile Tyr Lys Ala Ile Ser Glu Leu Asp Ile Leu Leu
145                 150                 155                 160

Ser Trp Ile Lys Lys Leu Leu Glu Ser Ser Gln
                165                 170

<210> SEQ ID NO 3
<211> LENGTH: 179
<212> TYPE: PRT
<213> ORGANISM: Equine Herpes Virus

<400> SEQUENCE: 3

Met Phe Arg Ala Ser Leu Leu Cys Cys Leu Val Leu Leu Ala Gly Val
 1               5                  10                  15

Trp Ala Asp Asn Lys Tyr Asp Ser Glu Ser Gly Asp Asp Cys Pro Thr
            20                  25                  30

Leu Pro Thr Ser Leu Pro His Met Leu His Glu Leu Arg Ala Ala Phe
        35                  40                  45

Ser Arg Val Lys Thr Phe Phe Gln Met Lys Asp Gln Leu Asp Asn Met
 50                  55                  60

Leu Leu Asp Gly Ser Leu Leu Glu Asp Phe Lys Gly Tyr Leu Gly Cys
 65                  70                  75                  80

Gln Ala Leu Ser Glu Met Ile Gln Phe Tyr Leu Glu Glu Val Met Pro
                85                  90                  95

Gln Ala Glu Asn His Ser Thr Asp Gln Glu Lys Asp Lys Val Asn Ser
            100                 105                 110

Leu Gly Glu Lys Leu Lys Thr Leu Arg Val Arg Leu Arg Arg Cys His
        115                 120                 125

Arg Phe Leu Pro Cys Glu Asn Lys Ser Lys Ala Val Glu Gln Val Lys
130                 135                 140

Ser Ala Phe Ser Lys Leu Gln Glu Lys Gly Val Tyr Lys Ala Met Ser
145                 150                 155                 160

Glu Phe Asp Ile Phe Ile Asn Tyr Ile Glu Ala Tyr Met Thr Thr Lys
                165                 170                 175

Met Lys Asn

<210> SEQ ID NO 4
<211> LENGTH: 170
<212> TYPE: PRT
<213> ORGANISM: Epstein Barr Virus
```

```
<400> SEQUENCE: 4

Met Glu Arg Arg Leu Val Val Thr Leu Gln Cys Leu Val Leu Leu Tyr
1               5                   10                  15

Leu Ala Pro Glu Cys Gly Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Val Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ala Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Lys
        115                 120                 125

Ser Lys Ala Val Glu Gln Ile Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170

<210> SEQ ID NO 5
<211> LENGTH: 178
<212> TYPE: PRT
<213> ORGANISM: Mus musculus

<400> SEQUENCE: 5

Met Pro Gly Ser Ala Leu Leu Cys Cys Leu Leu Leu Leu Thr Gly Met
1               5                   10                  15

Arg Ile Ser Arg Gly Gln Tyr Ser Arg Glu Asp Asn Asn Cys Thr His
            20                  25                  30

Phe Pro Val Gly Gln Ser His Met Leu Leu Glu Leu Arg Thr Ala Phe
        35                  40                  45

Ser Gln Val Lys Thr Phe Phe Gln Thr Lys Asp Gln Leu Asp Asn Ile
    50                  55                  60

Leu Leu Thr Asp Ser Leu Met Gln Asp Phe Lys Gly Tyr Leu Gly Cys
65                  70                  75                  80

Gln Ala Leu Ser Glu Met Ile Gln Phe Tyr Leu Val Glu Val Met Pro
                85                  90                  95

Gln Ala Glu Lys His Gly Pro Glu Ile Lys Glu His Leu Asn Ser Leu
            100                 105                 110

Gly Glu Lys Leu Lys Thr Leu Arg Met Arg Leu Arg Arg Cys His Arg
        115                 120                 125

Phe Leu Pro Cys Glu Asn Lys Ser Lys Ala Val Glu Gln Val Lys Ser
    130                 135                 140

Asp Phe Asn Lys Leu Gln Asp Gln Gly Val Tyr Lys Ala Met Asn Glu
145                 150                 155                 160

Phe Asp Ile Phe Ile Asn Cys Ile Glu Ala Tyr Met Met Ile Lys Met
                165                 170                 175

Lys Ser
```

-continued

```
<210> SEQ ID NO 6
<211> LENGTH: 178
<212> TYPE: PRT
<213> ORGANISM: Homo sapiens

<400> SEQUENCE: 6

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 7
<211> LENGTH: 20
<212> TYPE: DNA
<213> ORGANISM: Artificial Sequence
<220> FEATURE:
<223> OTHER INFORMATION: IL-8 forward.
<220> FEATURE:
<221> NAME/KEY: misc_feature
<222> LOCATION: (1)..(20)
<223> OTHER INFORMATION: IL-8 forward probe

<400> SEQUENCE: 7
tggcagcctt cctgatttct                                              20

<210> SEQ ID NO 8
<211> LENGTH: 26
<212> TYPE: DNA
<213> ORGANISM: Artificial Sequence
<220> FEATURE:
<223> OTHER INFORMATION: IL-8 reverse.
<220> FEATURE:
<221> NAME/KEY: misc_feature
<222> LOCATION: (1)..(26)
<223> OTHER INFORMATION: IL-8 reverse probe.

<400> SEQUENCE: 8
tgcactgaca tctaagttct ttagca                                       26

<210> SEQ ID NO 9
<211> LENGTH: 28
<212> TYPE: DNA
```

<213> ORGANISM: Artificial Sequence
<220> FEATURE:
<223> OTHER INFORMATION: IL-8 probe.
<220> FEATURE:
<221> NAME/KEY: misc_feature
<222> LOCATION: (1)..(28)
<223> OTHER INFORMATION: IL-8 probe.

<400> SEQUENCE: 9
tggcaaaact gcaccttcac acagagct                      28

<210> SEQ ID NO 10
<211> LENGTH: 21
<212> TYPE: DNA
<213> ORGANISM: Artificial Sequence
<220> FEATURE:
<223> OTHER INFORMATION: IL-10 forward.
<220> FEATURE:
<221> NAME/KEY: misc_feature
<222> LOCATION: (1)..(21)
<223> OTHER INFORMATION: IL-10 forward.

<400> SEQUENCE: 10
gagatctccg agatgccttc a                             21

<210> SEQ ID NO 11
<211> LENGTH: 26
<212> TYPE: DNA
<213> ORGANISM: Artificial Sequence
<220> FEATURE:
<223> OTHER INFORMATION: IL-10 reverse.
<220> FEATURE:
<221> NAME/KEY: misc_feature
<222> LOCATION: (1)..(26)
<223> OTHER INFORMATION: IL-10 reverse.

<400> SEQUENCE: 11
caaggactcc tttaacaaca agttgt                        26

<210> SEQ ID NO 12
<211> LENGTH: 33
<212> TYPE: DNA
<213> ORGANISM: Artificial Sequence
<220> FEATURE:
<223> OTHER INFORMATION: IL-10 probe.
<220> FEATURE:
<221> NAME/KEY: misc_feature
<222> LOCATION: (1)..(33)
<223> OTHER INFORMATION: IL-10 probe.

<400> SEQUENCE: 12
tgaagacttt ctttcaaatg aaggatcagc tgg                33

<210> SEQ ID NO 13
<211> LENGTH: 20
<212> TYPE: DNA
<213> ORGANISM: Artificial Sequence
<220> FEATURE:
<223> OTHER INFORMATION: ICAM-1 forward.
<220> FEATURE:
<221> NAME/KEY: misc_feature
<222> LOCATION: (1)..(20)
<223> OTHER INFORMATION: ICAM-1 forward.

<400> SEQUENCE: 13
gccaggagac actgcagaca                               20

<210> SEQ ID NO 14
<211> LENGTH: 21

```
<212> TYPE: DNA
<213> ORGANISM: Artificial Sequence
<220> FEATURE:
<223> OTHER INFORMATION: ICAM-reverse.
<220> FEATURE:
<221> NAME/KEY: misc_feature
<222> LOCATION: (1)..(21)
<223> OTHER INFORMATION: ICAM reverse.

<400> SEQUENCE: 14
tggcttcgtc agaatcacgt t                                             21

<210> SEQ ID NO 15
<211> LENGTH: 24
<212> TYPE: DNA
<213> ORGANISM: Artificial Sequence
<220> FEATURE:
<223> OTHER INFORMATION: ICAM-1 probe.
<220> FEATURE:
<221> NAME/KEY: misc_feature
<222> LOCATION: (1)..(24)
<223> OTHER INFORMATION: ICAM-1 probe.

<400> SEQUENCE: 15
tgaccatcta cagctttccg gcgc                                          24

<210> SEQ ID NO 16
<211> LENGTH: 20
<212> TYPE: DNA
<213> ORGANISM: Artificial Sequence
<220> FEATURE:
<223> OTHER INFORMATION: ICAM-2 forward.
<220> FEATURE:
<221> NAME/KEY: misc_feature
<222> LOCATION: (1)..(20)
<223> OTHER INFORMATION: ICAM-2 forward.

<400> SEQUENCE: 16
cgggaagcag gagtcaatga                                               20

<210> SEQ ID NO 17
<211> LENGTH: 20
<212> TYPE: DNA
<213> ORGANISM: Artificial Sequence
<220> FEATURE:
<223> OTHER INFORMATION: ICAM-2 reverse.
<220> FEATURE:
<221> NAME/KEY: misc_feature
<222> LOCATION: (1)..(20)
<223> OTHER INFORMATION: ICAM-2 reverse.

<400> SEQUENCE: 17
gggttgcagt gtcaggatga                                               20

<210> SEQ ID NO 18
<211> LENGTH: 24
<212> TYPE: DNA
<213> ORGANISM: Artificial Sequence
<220> FEATURE:
<223> OTHER INFORMATION: ICAM-2 probe.
<220> FEATURE:
<221> NAME/KEY: misc_feature
<222> LOCATION: (1)..(24)
<223> OTHER INFORMATION: ICAM-2 probe.

<400> SEQUENCE: 18
tcagcgtgta ccagcctcca aggc                                          24

<210> SEQ ID NO 19
```

```
<211> LENGTH: 22
<212> TYPE: DNA
<213> ORGANISM: Artificial Sequence
<220> FEATURE:
<223> OTHER INFORMATION: B7-H1 forward.
<220> FEATURE:
<221> NAME/KEY: misc_feature
<222> LOCATION: (1)..(22)
<223> OTHER INFORMATION: B7H1 forward.
<220> FEATURE:
<221> NAME/KEY: misc_feature
<222> LOCATION: (1)..(22)
<223> OTHER INFORMATION: B7-H1 forward.

<400> SEQUENCE: 19
gctgaattgg tcatcccaga ac                                        22

<210> SEQ ID NO 20
<211> LENGTH: 22
<212> TYPE: DNA
<213> ORGANISM: Artificial Sequence
<220> FEATURE:
<223> OTHER INFORMATION: B7-H1 reverse.
<220> FEATURE:
<221> NAME/KEY: misc_feature
<222> LOCATION: (1)..(22)
<223> OTHER INFORMATION: B7-H1 reverse.

<400> SEQUENCE: 20
gatggctccc agaattacca ag                                        22

<210> SEQ ID NO 21
<211> LENGTH: 29
<212> TYPE: DNA
<213> ORGANISM: Artificial Sequence
<220> FEATURE:
<223> OTHER INFORMATION: B7-H1 probe.
<220> FEATURE:
<221> NAME/KEY: misc_feature
<222> LOCATION: (1)..(29)
<223> OTHER INFORMATION: B7-H1 probe.

<400> SEQUENCE: 21
tctggcacat cctccaaatg aaaggactc                                 29
```